(12) United States Patent
Komatsu et al.

(10) Patent No.: US 8,496,563 B2
(45) Date of Patent: Jul. 30, 2013

(54) EXERCISE SUPPORT APPARATUS, COMPUTER READABLE STORAGE MEDIUM RECORDING A COMPUTER PROGRAM, AND EXERCISE SUPPORT METHOD

(75) Inventors: Yoshiaki Komatsu, Yokkaichi (JP); Kazuyuki Sato, Tokyo-to (JP)

(73) Assignees: Brother Kogyo Kabushiki Kaisha, Nagoya-shi, Aichi-ken (JP); Kabushiki Kaisha Xing, Nagoya-shi, Aichi-ken (JP)

( * ) Notice: Subject to any disclaimer, the term of this patent is extended or adjusted under 35 U.S.C. 154(b) by 316 days.

(21) Appl. No.: 12/870,293

(22) Filed: Aug. 27, 2010

(65) Prior Publication Data

US 2010/0323846 A1 Dec. 23, 2010

Related U.S. Application Data

(63) Continuation-in-part of application No. PCT/JP2009/053551, filed on Feb. 26, 2009.

(30) Foreign Application Priority Data

Feb. 27, 2008 (JP) ................................. 2008-046611
Feb. 24, 2009 (JP) ................................. 2009-041229

(51) Int. Cl.
*A63B 71/00* (2006.01)
(52) U.S. Cl.
USPC ................................................. 482/9; 482/1
(58) Field of Classification Search
USPC ....................................................... 482/1–9
See application file for complete search history.

(56) References Cited

U.S. PATENT DOCUMENTS

| | | | | |
|---|---|---|---|---|
| 5,890,997 A | * | 4/1999 | Roth | 482/8 |
| 7,761,300 B2 | * | 7/2010 | Klingler | 704/260 |
| 8,001,472 B2 | * | 8/2011 | Gilley et al. | 715/716 |
| 8,066,514 B2 | * | 11/2011 | Clarke | 434/247 |
| 8,128,532 B2 | * | 3/2012 | Chen et al. | 482/8 |
| 2003/0017914 A1 | * | 1/2003 | Jackowski | 482/9 |
| 2004/0248713 A1 | * | 12/2004 | Campanaro et al. | 482/123 |
| 2005/0164833 A1 | * | 7/2005 | Florio | 482/9 |

(Continued)

FOREIGN PATENT DOCUMENTS

| | | |
|---|---|---|
| JP | 2000-51390 | 2/2000 |
| JP | 2003-216739 | 7/2003 |

(Continued)

OTHER PUBLICATIONS

International Search Report dated May 19, 2009.

(Continued)

*Primary Examiner* — Loan Thanh
*Assistant Examiner* — Sundhara Ganesan
(74) *Attorney, Agent, or Firm* — Scully, Scott, Murphy & Presser, PC

(57) ABSTRACT

An exercise support apparatus comprising acquiring unit for acquiring first information representative of at least one of an exercise experience and physical fitness of a user, storing unit for storing a plurality of kinds of exercises, exercise selecting unit configured to select at least one of the exercises stored in the storing unit, and at least one break; and exercise menu generating unit configured to generate an exercise menu including the selected exercises and the at least one break based on the acquired first information by the acquiring unit.

10 Claims, 23 Drawing Sheets

| SESSION NAME | CONTENT NAME | PRESENTATION TIME | SEQUENCE NUMBER | SONG TITLE |
|---|---|---|---|---|
| WARMING-UP | WARMING-UP | 300 | 1 | SONG TITLE1 |
| FIRST CIRCUIT | BREAK | 10 | 2 | SONG TITLE2 |
| | AEROBIC1 | 30 | 3 | |
| | BREAK | 5 | 4 | |
| | ANAEROBIC1 | 35 | 5 | |
| | BREAK | 10 | 6 | |
| | AEROBIC2 | 30 | 7 | |
| | BREAK | 5 | 8 | |
| | ANAEROBIC2 | 35 | 9 | |
| | BREAK | 10 | 10 | |
| | AEROBIC3 | 30 | 11 | |
| | BREAK | 5 | 12 | |
| | ANAEROBIC3 | 35 | 13 | |
| | BREAK | 10 | 14 | |
| | AEROBIC4 | 30 | 15 | |
| | BREAK | 5 | 16 | |
| | ANAEROBIC4 | 35 | 17 | |
| SECOND CIRCUIT | ⋮ | ⋮ | 18 ⋮ | SONG TITLE2 |
| THIRD CIRCUIT | ⋮ | ⋮ | 34 ⋮ | SONG TITLE2 |
| FOURTH CIRCUIT | ⋮ | ⋮ | 50 ⋮ | SONG TITLE2 |
| COOL DOWN | STRETCH | 50 | 66 | SONG TITLE3 |
| | DEEP BREATHING | 60 | 67 | |

U.S. PATENT DOCUMENTS

| | | | |
|---|---|---|---|
| 2005/0202934 A1* | 9/2005 | Olrik et al. | 482/8 |
| 2006/0189440 A1* | 8/2006 | Gravagne | 482/8 |
| 2006/0234832 A1* | 10/2006 | Toyama et al. | 482/9 |
| 2006/0252602 A1* | 11/2006 | Brown et al. | 482/9 |
| 2007/0105629 A1 | 5/2007 | Toyama | |
| 2007/0135264 A1* | 6/2007 | Rosenberg | 482/8 |
| 2008/0220941 A1* | 9/2008 | Shaw et al. | 482/9 |

FOREIGN PATENT DOCUMENTS

| | | |
|---|---|---|
| JP | 2003-260160 | 9/2003 |
| JP | 2005-66185 | 3/2005 |
| JP | 2006-122343 | 5/2006 |
| JP | 2006-255028 | 9/2006 |
| JP | 2006-263002 | 10/2006 |
| JP | 2007-125251 | 5/2007 |

OTHER PUBLICATIONS

Japanese Official Action dated Feb. 26, 2013 from related application JP 2009-041229 together with a partial English language translation.

* cited by examiner

FIG. 9

| | EXERCISE EXPERIENCE VALUE AND PHYSICAL FITNESS VALUE 105c | | |
|---|---|---|---|
| | 1 | 2 | 3 |
| RATIO | 15/25 | 10/30 | 5/35 |

FIG. 10

| PERSONAL IDENTIFICATION INFORMATION | | XX-1234 |
|---|---|---|
| EXERCISE HABIT VALUE | | 3 |
| AGE | | 27 |
| SEX | | FEMALE |
| NORMAL HEART RATE | | 50 |
| WORK EXPERIENCE VALUE | AEROBIC DANCING | 3 |
| | HIP HOP | 2 |
| | LATIN DANCE | 1 |

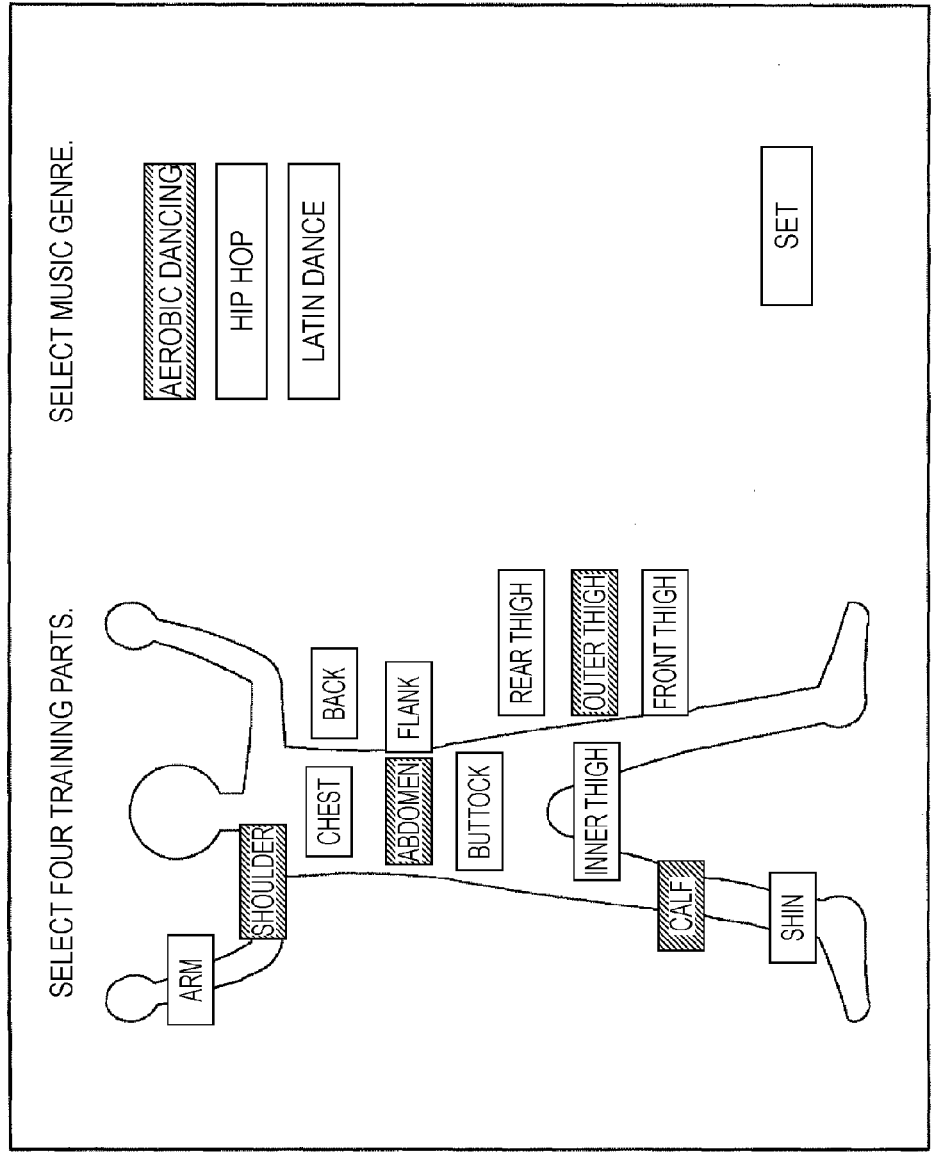

FIG. 12

| SESSION NAME | CONTENT NAME | PRESENTATION TIME | SEQUENCE NUMBER | SONG TITLE |
|---|---|---|---|---|
| WARMING-UP | WARMING-UP | 300 | 1 | SONG TITLE1 |
| FIRST CIRCUIT | BREAK | 10 | 2 | SONG TITLE2 |
| | AEROBIC1 | 30 | 3 | |
| | BREAK | 5 | 4 | |
| | ANAEROBIC1 | 35 | 5 | |
| | BREAK | 10 | 6 | |
| | AEROBIC2 | 30 | 7 | |
| | BREAK | 5 | 8 | |
| | ANAEROBIC2 | 35 | 9 | |
| | BREAK | 10 | 10 | |
| | AEROBIC3 | 30 | 11 | |
| | BREAK | 5 | 12 | |
| | ANAEROBIC3 | 35 | 13 | |
| | BREAK | 10 | 14 | |
| | AEROBIC4 | 30 | 15 | |
| | BREAK | 5 | 16 | |
| | ANAEROBIC4 | 35 | 17 | |
| SECOND CIRCUIT | ⋮ | ⋮ | 18 ⋮ | SONG TITLE2 |
| THIRD CIRCUIT | ⋮ | ⋮ | 34 ⋮ | SONG TITLE2 |
| FOURTH CIRCUIT | ⋮ | ⋮ | 50 ⋮ | SONG TITLE2 |
| COOL DOWN | STRETCH | 50 | 66 | SONG TITLE3 |
| | DEEP BREATHING | 60 | 67 | |

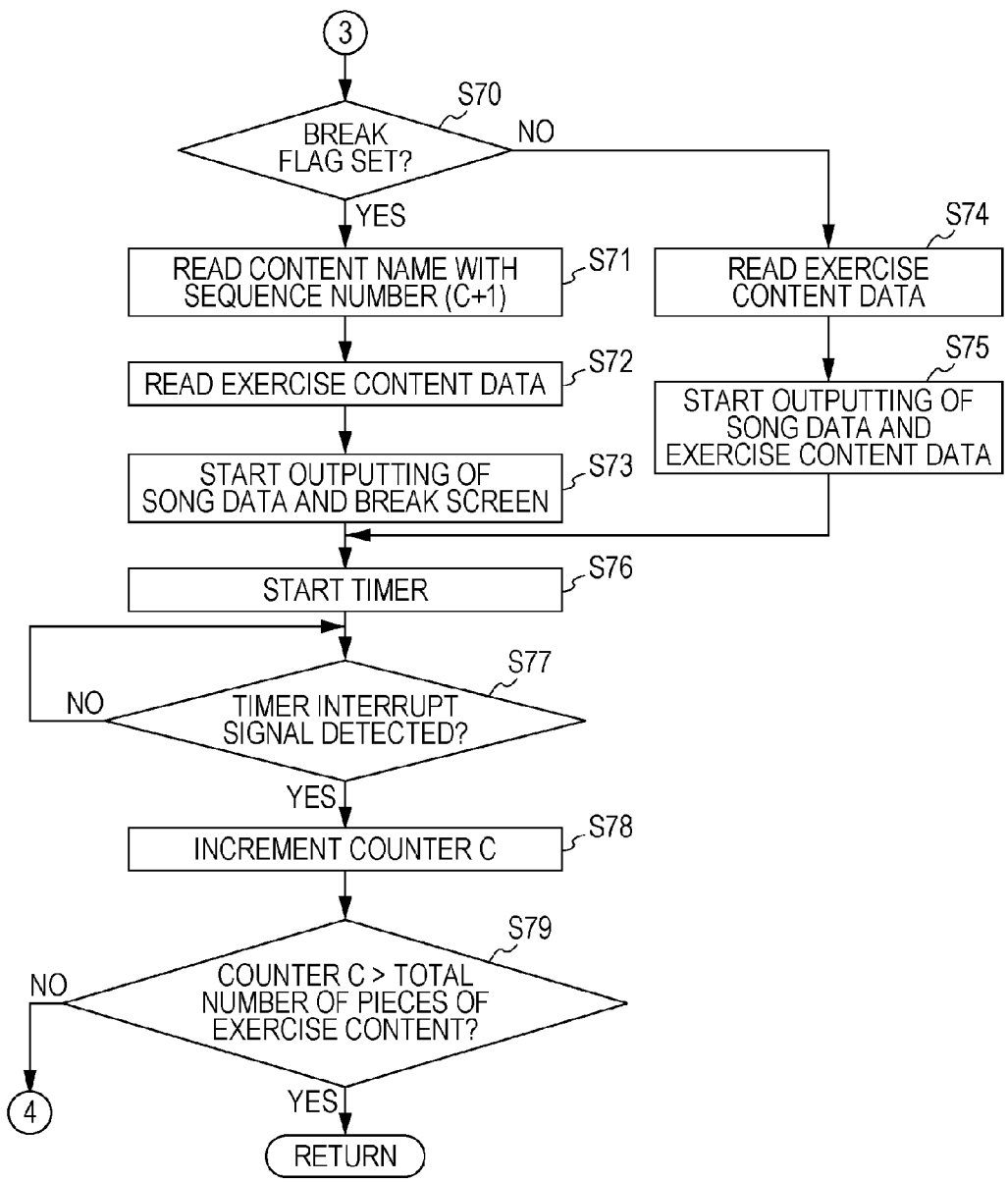

FIG. 24

| SESSION NAME | CONTENT NAME | PRESENTATION TIME | SEQUENCE NUMBER | SONG TITLE |
|---|---|---|---|---|
| WARMING-UP | WARMING-UP | 300 | 1 | SONG TITLE1 |
| FIRST CIRCUIT | AEROBIC1 | 30 | 2 | SONG TITLE2 |
| | BREAK | 10 | 3 | |
| | ANAEROBIC1 | 35 | 4 | |
| | BREAK | 5 | 5 | |
| | AEROBIC2 | 30 | 6 | |
| | BREAK | 10 | 7 | |
| | ANAEROBIC2 | 35 | 8 | |
| | BREAK | 5 | 9 | |
| | AEROBIC3 | 30 | 10 | |
| | BREAK | 10 | 11 | |
| | ANAEROBIC3 | 35 | 12 | |
| | BREAK | 5 | 13 | |
| | AEROBIC4 | 30 | 14 | |
| | BREAK | 10 | 15 | |
| | ANAEROBIC4 | 35 | 16 | |
| | BREAK | 5 | 17 | |
| SECOND CIRCUIT | ⋮ | ⋮ | 18 ⋮ | SONG TITLE2 |
| THIRD CIRCUIT | ⋮ | ⋮ | 34 ⋮ | SONG TITLE2 |
| FOURTH CIRCUIT | ⋮ | ⋮ | 50 ⋮ | SONG TITLE2 |
| COOL DOWN | STRETCH | 50 | 66 | SONG TITLE3 |
| | DEEP BREATHING | 60 | 67 | |

EXERCISE SUPPORT APPARATUS, COMPUTER READABLE STORAGE MEDIUM RECORDING A COMPUTER PROGRAM, AND EXERCISE SUPPORT METHOD

CROSS REFERENCE TO RELATED APPLICATIONS

The present application is a Continuation-in-Part of International Application PCT/JP2009/053551 filed on Feb. 26, 2009, which claims the benefits of Japanese Patent Application No. 2009-041229 filed on Feb. 24, 2009, and Japanese Patent Application No. 2008-046611 filed on Feb. 27, 2008.

BACKGROUND OF THE INVENTION

Field of the Invention

The present invention relates to an exercise support apparatus, a recording medium recording a computer program, an exercise support system, and an exercise support method, which present a circuit exercise menu including breaks, aerobic exercises, and anaerobic exercises in accordance with the exercise experience and physical fitness of the user.

Recently, in indoor exercising mainly aimed at health promotion such as day-to-day physical conditioning and dieting, it is considered important to do moderate exercise suited to the exercise experience, physical fitness, and the like of the user in a continuous fashion, rather than doing excessive exercise at once. However, to provide a personalized exercise plan suited to each individual user, there is a need for an instructor who assigns a type and amount of exercise suited to the user's exercise experience, physical fitness, and the like. Consequently, not only is there a financial burden, such as personnel expenses related to the instructor, but also it is often difficult to choose a training time slot freely to suit everyone's schedule.

SUMMARY OF THE INVENTION

Circuit exercise plans which alternate between aerobic exercises such as a step exercise and anaerobic exercises such as muscular training have been increasingly introduced in recent years as being effective in promoting health. In some circuit exercise plans, anaerobic exercises for training one of the left and right muscles are instructed alternately with aerobic exercises or the like therebetween. Such circuit exercise plans are structured so that the amounts of exercise with respect to the left and right muscles are substantially equal throughout the presentation period of the circuit exercise plan, and a break is provided between each anaerobic exercise and each aerobic exercise to prevent injury and increase the exercise effect.

In the past, there have been documented exercise support apparatuses which manage personal information such as the exercise experience and physical fitness of each user, generate an exercise plan suited to each user, and present the generated exercise plan to the user by outputting a picture or image, and sound.

However, in the exercise support apparatuses according to the related art mentioned above, when a circuit exercise plan is adjusted to an amount of exercise suited to the user's exercise experience and physical fitness, the presentation period of the exercise plan changes. This changed presentation period may not match the exercise time previously planned by the user Consequently, to finish exercising within an exercise period previously planned by the user, it may become necessary to end the exercise without completion of the plan. Therefore, for example, there is a fear that the amounts of exercise with respect to the left and right muscles will be unequal.

In addition, with the exercise support apparatuses according to the related art mentioned above, it is difficult to change the break time included in the circuit exercise plan in accordance with the user's exercise experience and physical fitness. Consequently, there is a fear that injuries to the muscles are caused due to fatigue and a decrease in the exercise effect of each exercise occurs while the user is doing the circuit exercise.

The present invention has been made in view of the above circumstances, and accordingly it is an object of the present invention to provide an exercise support apparatus which makes it possible to present an exercise menu representing an exercise plan that provides a high exercise effect and facilitates recovery from fatigue to prevent injury during exercise by setting breaks according to the exercise experience and physical fitness of each user, a computer readable storage medium recording a computer program, and an exercise support method.

An exercise support apparatus according to the present invention includes acquiring unit for acquiring first information representative of at least one of an exercise experience and physical fitness of a user; storing unit for storing a plurality of kinds of exercises; exercise selecting unit configured to select at least one of the exercises stored in the storing unit, and at least one break; and exercise menu generating unit configured to generate an exercise menu including the selected exercises and the at least one break based on the acquired first information by acquiring unit.

A computer readable storage medium recording a program to be executed by the computer according to the present invention includes the program causing a computer to perform steps comprising acquiring first information representative of at least one of an exercise experience and physical fitness of a user; selecting at least one exercise of a plurality of kinds of exercises stored in storing unit, and at least one break; acquired first information by acquiring unit and generating an exercise menu including the selected exercises and the at least one break based on acquired first information by acquiring unit.

An exercise support method according to the present invention includes acquiring on a computer first information representative of at least one of an exercise experience and physical fitness; selecting from a selection window on the computer at least one exercise of a plurality of kinds of exercises stored in a storing unit, and at least one break; generating an exercise menu including the selected exercises and the at least one break based on acquired first information by acquiring unit.

BRIEF DESCRIPTION OF THE DRAWINGS

FIG. 9 is a chart showing an example of a ratio determination table;

FIG. 10 is a chart showing an example of the record layout of personal information;

FIG. 11 is a schematic diagram showing an example of a selection screen for training parts and a music genre;

FIG. 12 is a chart showing an example of the record layout of an exercise menu;

FIG. 23 is a flowchart showing the procedure of an exercise menu presentation process continued from FIG. 22;

FIG. 24 is a table showing another example of the record layout of an exercise menu;

DESCRIPTION OF THE PREFERRED EMBODIMENTS

Embodiment 1

Figure 1:
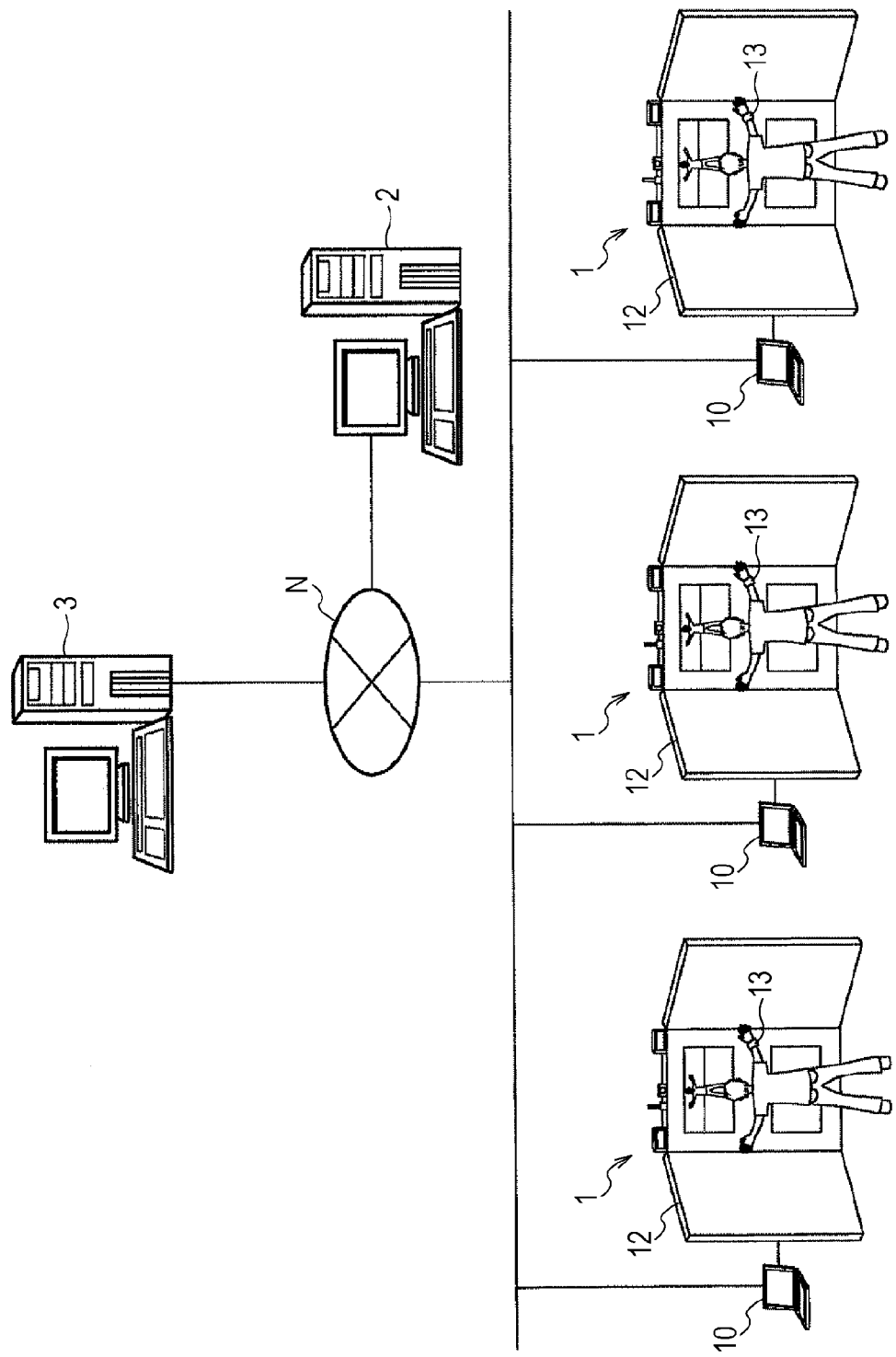
FIG. 1 is a schematic diagram showing the configuration of a system using an exercise support apparatus according to the present invention.

Hereinbelow, the present invention will be described specifically with reference to drawings illustrating its embodiments. In the drawings, reference numeral 1 denotes an exercise support apparatus which presents the user with the picture or image of each exercise constituting an exercise plan. As shown in FIG. 1, the exercise support apparatus 1 includes a control computer 10, a housing 12, and a heart rate sensing device 13 attached to the user's body 14. The control computer 10 of the exercise support apparatus 1 is connected so as to mutually transmit and receive data to and from a personal information management computer 2 that manages personal information, and a server computer 3 that distributes song data and the like to the control computer 10, via a communication network N such as a LAN (Local Area Network).

The server computer 3 includes a database (not shown) in which a plurality of pieces of song data made up of MIDI (Music Instrument Digital Interface) data or the like are stored in association with song titles and singer names. The server computer 3 reads song data from the database via the communication network N in response to a request signal from the control computer 10 of the exercise support apparatus 1. The personal information management computer 2 accepts the user's personal information, and manages the accepted personal information. The personal information management computer 2 is also configured to execute user authentication, transmission of personal information to the exercise support apparatus 1, and the like.

Figure 2:
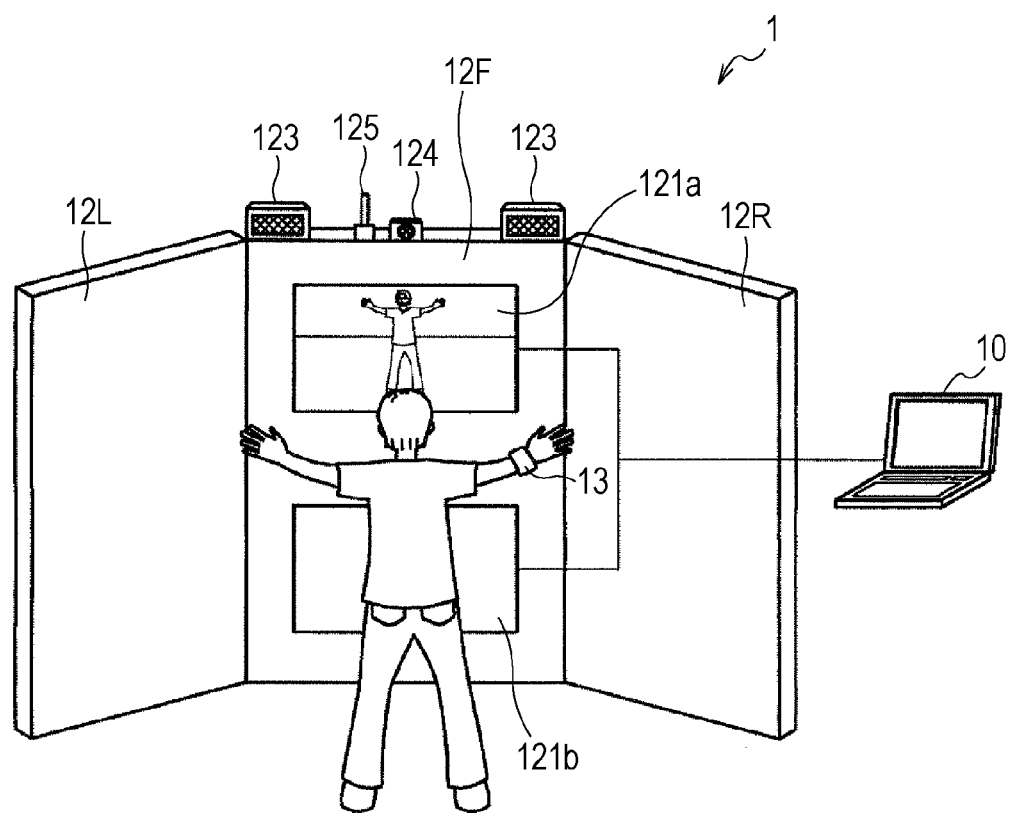
FIG. 2 is a schematic perspective view schematically showing the outward appearance of an exercise support apparatus.

As shown in FIG. 2, the housing 12 of the exercise support apparatus 1 is made up of three vertically elongated panels including a panel 12F standing upright directly in front of the user, a panel 12L standing upright diagonally to the left in front of the user, and a panel 12R standing upright diagonally to the right in front of the user. The housing 12 is so placed that the panel surfaces of the respective panel face the user. The panel surfaces of the panel 12L and the panel 12R are formed into mirror surfaces. The panel 12L and the panel 12R are so formed as to allow the user to view the whole body of the user himself/herself during exercise as reflected in the mirror surface. In the panel surface of the panel 12F, a first picture display unit 121a and a second picture display unit 121b each made up of a liquid crystal monitor or the like are installed so as to be aligned top and bottom. The first picture display unit 121a and the second picture display unit 121b may be an image display unit.

A sound output unit 123, an image capturing unit 124, and a sensor signal receiving unit 125 are provided on the upper surface of the panel 12F. The sound output unit 123 outputs sound. The sound output unit 123 is located at either end along the upper side of the panel surface of the panel 12F. The image capturing unit 124 is located at the center of the upper side of the panel surface. The image capturing unit 124 captures the image of the user's whole body. The heart rate sensing device 13 is attached to the user. The sensor signal receiving unit 125 receives a sensor signal wave from the heart rate sensing device 13. The heart rate sensing device 13 is worn on the user's wrist or the like. The heart rate sensing device 13 is configured to sense the user's heart rate at any time and transmit the heart rate to the sensor signal receiving unit 125.

The image capturing unit 124 is a digital camera or the like which captures the image of the user's whole body at any time and transmits an image capture signal to the control computer 10. The control computer 10 is configured to detect the user's posture from the image capture signal. The panel 12F includes the first picture display unit 121a and the second picture display unit 121b. The first picture display unit 121a and the second picture display unit 121b are positioned top and bottom directly in front of the user. A 3D image of an exercise instructor is displayed in accordance with the user's posture on one of the first picture display unit 121a and the second picture display unit 121b. The 3D image of the exercise instructor is generated from picture or image content. The sound output unit 123 is positioned above to the left and right of the user. Sound from the 3D image of the exercise instructor is generated from the picture or image content, and a song whose tempo is synchronized with the rhythm of the instructed exercise are outputted from the sound output unit 123.

The first picture display unit 121a, the second picture display unit 121b, and the sound output unit 123 constitute presenting means for presenting the picture or image of each exercise constituting an exercise menu. The user exercises while imitating the movements of a 3D image of the exercise instructor displayed on the first picture display unit 121a or the second picture display unit 121b. Also, the user exercises in accordance with an instruction and the tempo of a song based on the sound outputted from the sound output unit 123. The user performs an exercise presented by the exercise support apparatus 1 while looking at the image of his/her own figure reflected in the mirror surface of each of the panel 12L and the panel 12R.

Figure 3:
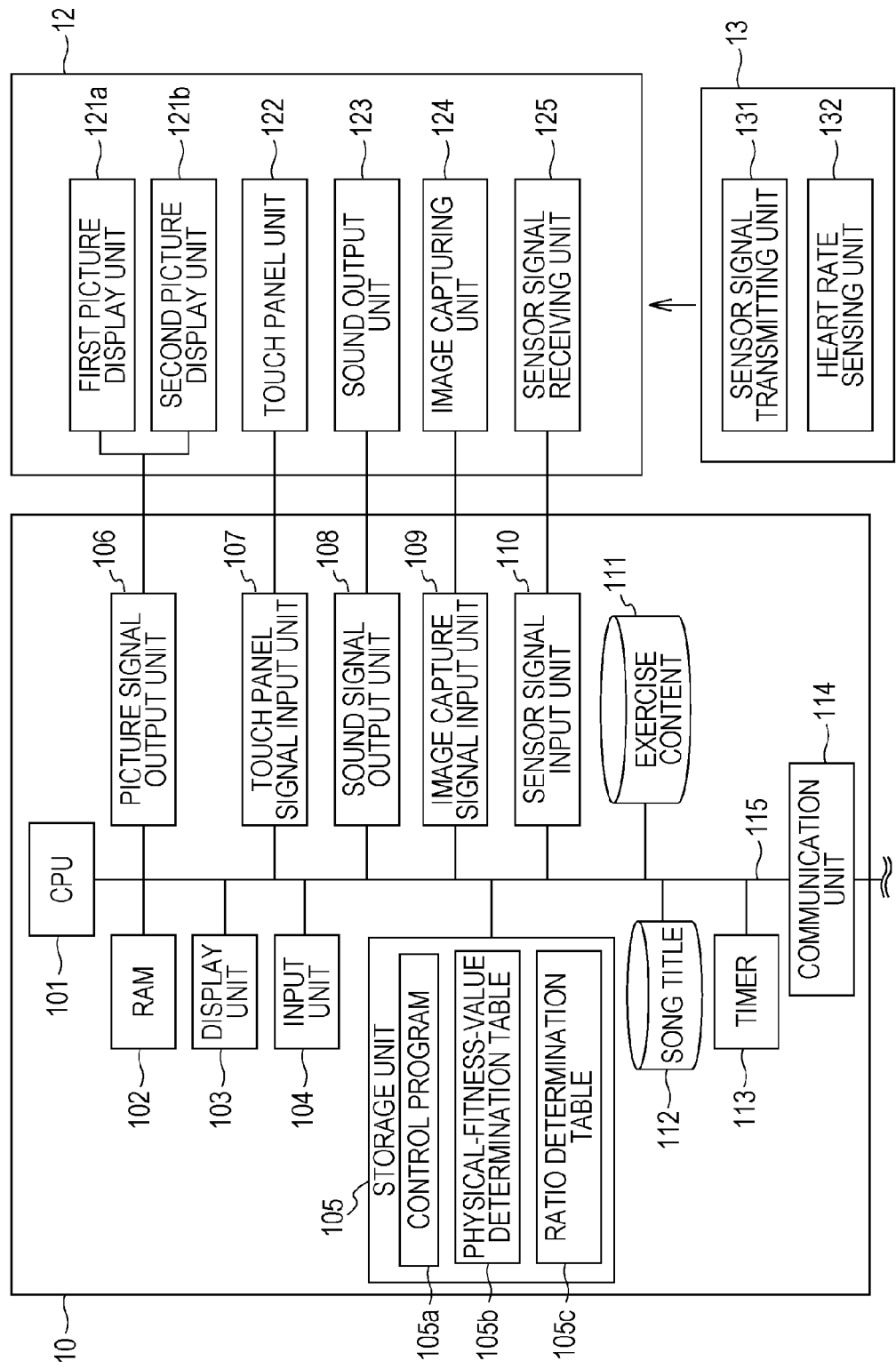
FIG. 3 is a block diagram showing the internal configuration of an exercise support apparatus according to Embodiment 1.

As shown in FIG. 3, the control computer 10 includes a CPU (Central Processing Unit) 101 as a control unit, a RAM (Random Access Memory) 102, a display unit 103, an input unit 104, a storage unit 105, and a communication unit 114. The display unit 103 is made up of a liquid crystal display or the like. The input unit 104 is made up of a keyboard and a mouse, or the like. The storage unit 105 is made up of a ROM (Read-Only Memory) and a non-volatile memory such as a flash memory. The exercise times (not shown) of exercises such as a warming-up exercise, a circuit exercise, a stretch exercise, and a deep breathing exercise are set in advance and stored in the storage unit 105. The storage unit 105 includes a control program 105a, a physical-fitness-value determination table 105b, and a ratio determination table 105c. The communication unit 114 is a LAN card or the like, and transmits and receives various kinds of data to and from the personal information management computer 2 and the server computer 3 by a protocol such as the HTTP (Hyper Text Transfer Protocol) via the communication network N.

In addition, the control computer 10 includes an exercise content database 111. The exercise content database 111 is made up of individual pieces of exercise content data. Exercise content data represents each of the exercises from which an exercise menu representing the user's personalized exercise plan is generated and presented by the exercise support apparatus 1. The exercise content data is stored in the exercise content database 111 having a hierarchical structure. Exercise content data includes a 3D image of the exercise instructor that moves in accordance with an exercise, and its background image. The 3D image and its background image are each a picture or image drawn by computer graphics technology. Exercise content data may be made up of the above-described picture or image, and sound by which instructions are given to the user by a 3D image of an exercise instructor. Exercise content data stored in the exercise content database 111 is made up of polygon data, texture data, matrix data, background image data, sound data, and the like. The polygon data constitutes a 3D image of a person. The texture data is mapped to the surface of the 3D image. The matrix data is data for coordinate transformation.

In addition, the control computer 10 includes a picture or image signal output unit 106, a sound signal output unit 108, a touch panel signal input unit 107, an image capture signal input unit 109, a sensor signal input unit 110, a song title database 112, and a timer 113. The picture or image signal output unit 106 outputs each of a picture or image signal and a sound signal, which are generated on the basis of song data received from the server computer 3 via the communication unit 114, to the housing 12. A touch panel signal given from a touch panel unit 122 provided on the display surface of the first picture or image display unit 121a of the housing 12 is inputted to the touch panel signal input unit 107. An image capture signal from the image capturing unit 124 of the housing 12 is inputted to the image capture signal input unit 109.

A sensor signal from the sensor signal receiving unit 125 of the housing 12 is inputted to the sensor signal input unit 110. The song title database 112 is a database in which song titles are stored. The timer 113 performs a timing operation.

The touch panel unit 122 of the housing 12 acquires information on a position touched by the user in accordance with a selection screen described later displayed on the first picture display unit 121a. Then, the touch panel unit 122 outputs the information to the touch panel signal input unit 107 of the control computer 10 as a touch panel signal. The CPU 101 is configured to acquire an item selected by the user, by comparing position information with a selection screen. The position information represents the position indicated by the touch panel signal given from the touch panel signal input unit 107. The selection screen is the screen displayed on the first picture display unit 121a. The heart beat sensing device 13 includes a heart rate sensing unit 132 and a sensor signal transmitting unit 131. The heart rate sensing unit 132 senses the user's heart rate. The sensor signal transmitting unit 131 transmits information indicative of the sensed heart rate to the sensor signal receiving unit 125 of the housing 12 via a wireless LAN or the like. The CPU 101 is connected to individual hardware units of the control computer 10 via a bus 115. The CPU 101 controls the individual hardware units, and reads the control program 105a stored in the computer readable storage unit 105 into the RAM 102 and executes the control program 105a, thereby executing various software processing.

Figure 4:
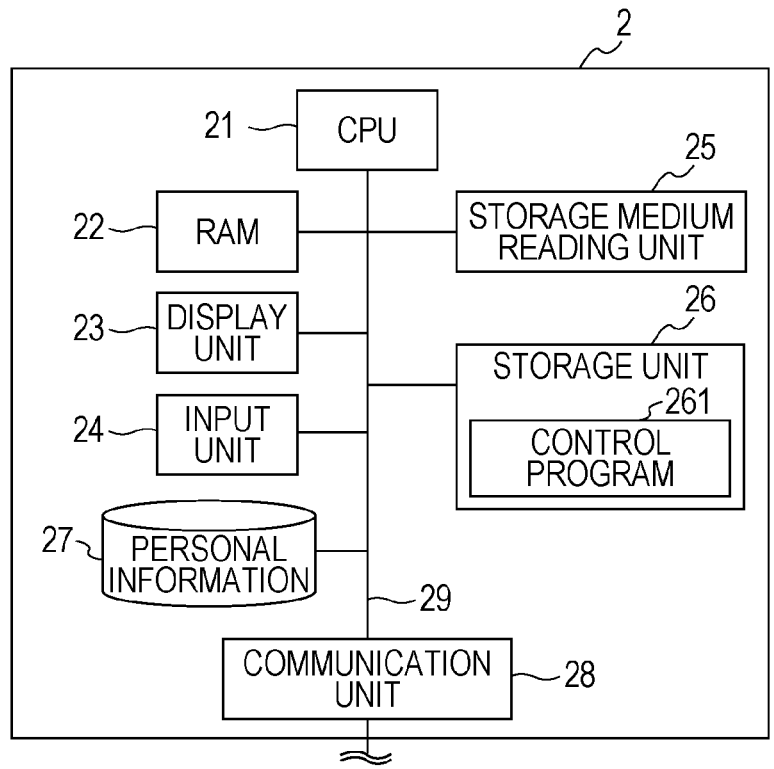
FIG. 4 is a block diagram showing the internal configuration of a personal information management computer.

As shown in FIG. 4, the personal information management computer 2 includes a CPU 21, a RAM 22, a display unit 23, an input unit 24, a storage medium reading unit 25, a storage unit 26, and a communication unit 28. The storage medium reading unit 25 reads stored information from a storage medium such as an IC card. The storage unit 26 is a computer readable storage medium that stores a control program 261. The communication unit 28 connects to the communication network N to transmit and receive data. In addition, the personal information management computer 2 includes a personal information database 27. The personal information database 27 includes identification information and authentication numbers or the like assigned to individual users. The personal information database 27 also stores the user's age, sex, and exercise experience or the like as attribute information in each piece of identification information. The CPU 21 is connected to individual hardware units of the personal information management computer 2 via a bus 29. The CPU 21 controls the individual hardware units, and reads the control program 261 stored in the storage unit 26 into the RAM 22 and executes the control program 261, thereby executing various software processing.

Figure 5:
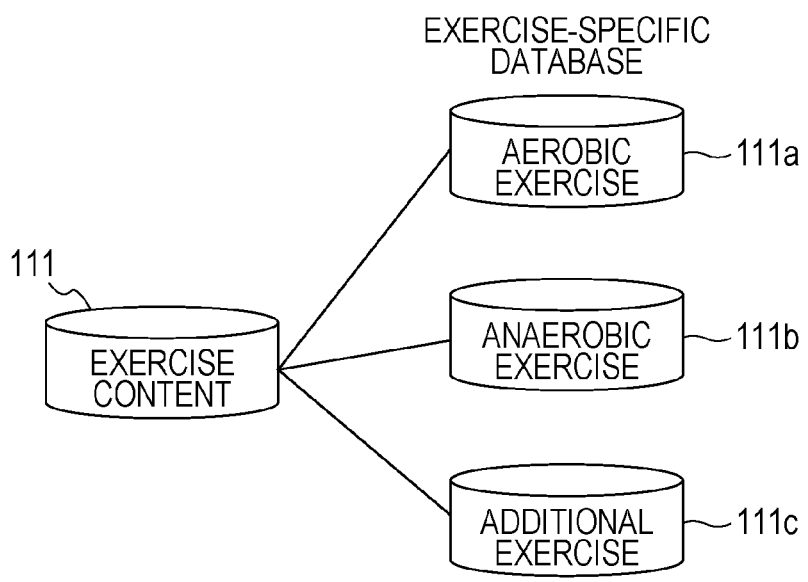
FIG. 5 is a schematic diagram showing the configuration of an exercise content database.

As shown in FIG. 5, the exercise content database 111 is made up of three exercise-specific databases including an aerobic exercise database 111a, an anaerobic exercise database 111b, and an additional exercise database 111c. The aerobic exercise database 111a stores data indicative of aerobic exercise content for instructing on aerobic exercises included in a circuit exercise. The anaerobic exercise database 111b stores data indicative of anaerobic exercise content for instructing on anaerobic exercises included in a circuit exercise.

The additional exercise database 111c stores exercise content indicative of additional exercises added to a circuit exercise. That is, the additional exercise database 111c may store data indicative of warming-up exercise content, stretch exercise content, and deep breathing exercise content. Warming-up exercise content is exercise content for instructing a warming-up exercise. A stretch exercise is included in a cool down exercise. Deep breathing exercise content is content for instructing a deep breathing exercise. Aerobic exercise content is exercise content for instructing on aerobic exercises (e.g., stepping exercise and jogging) that are exercises for producing muscular contraction energy mainly by the method of consuming oxygen. Anaerobic exercise content is exercise content for instructing on anaerobic exercises (e.g., push-ups) that produce mainly muscular contraction energy rather than oxygen consumption to promote development of muscles.

Figure 6:
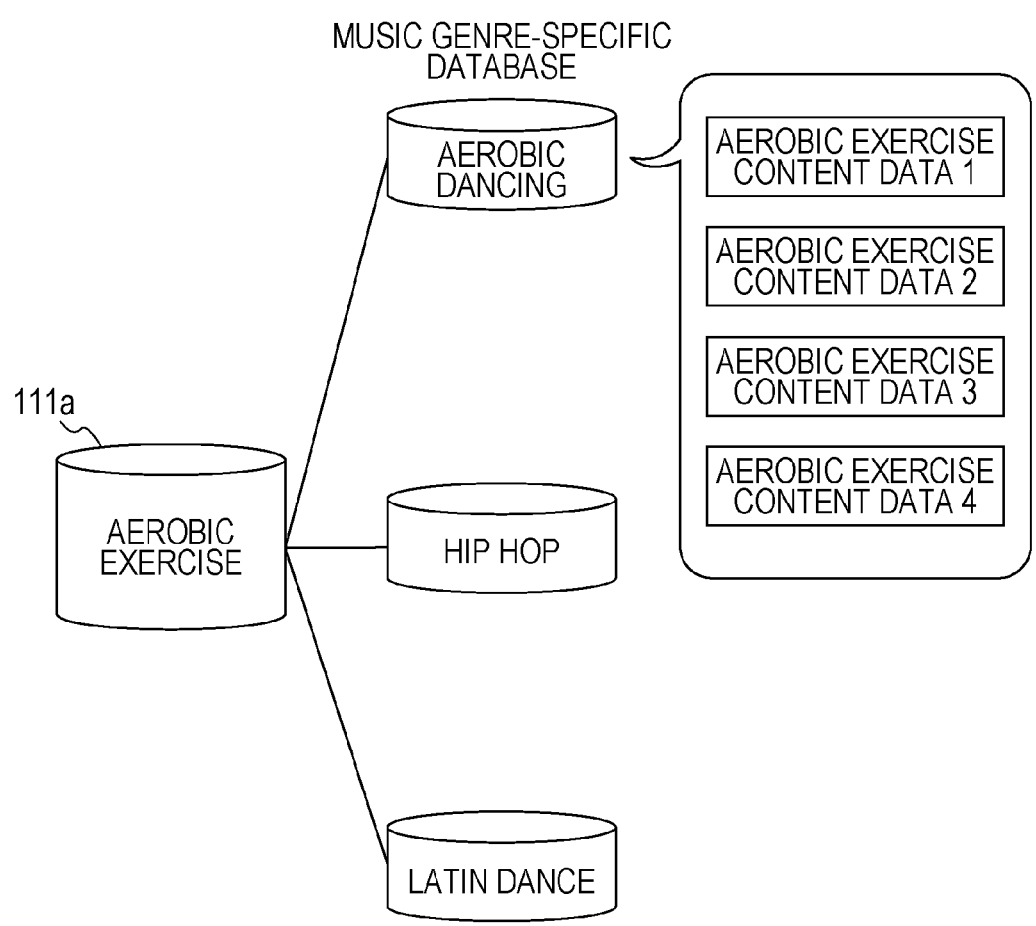
FIG. 6 is a schematic diagram showing the configuration of an aerobic exercise database.

As shown in FIG. 6, the aerobic exercise database 111a may be made up of three kinds of music genre-specific databases "aerobic dancing", "hip hop" and "Latin dance". Each music genre-specific database may store four kinds of aerobic exercise content data from Aerobic Exercise Content Data 1 to Aerobic Exercise Content Data 4 based on each corresponding music genre, together with their respective content names.

The anaerobic exercise database 111b may store 13 kinds of anaerobic exercise content data corresponding to respective training parts "shoulder", "arm", "chest", "back", "abdomen", "flank", "buttock", "inner thigh", "outer thigh", "front thigh", "back thigh", "calf", and "shin", together with their respective content names. The additional exercise database 111c may store warming-up exercise content data, stretch exercise content data, and deep breathing exercise content data, together with their respective content names.

Figures 7, 8:
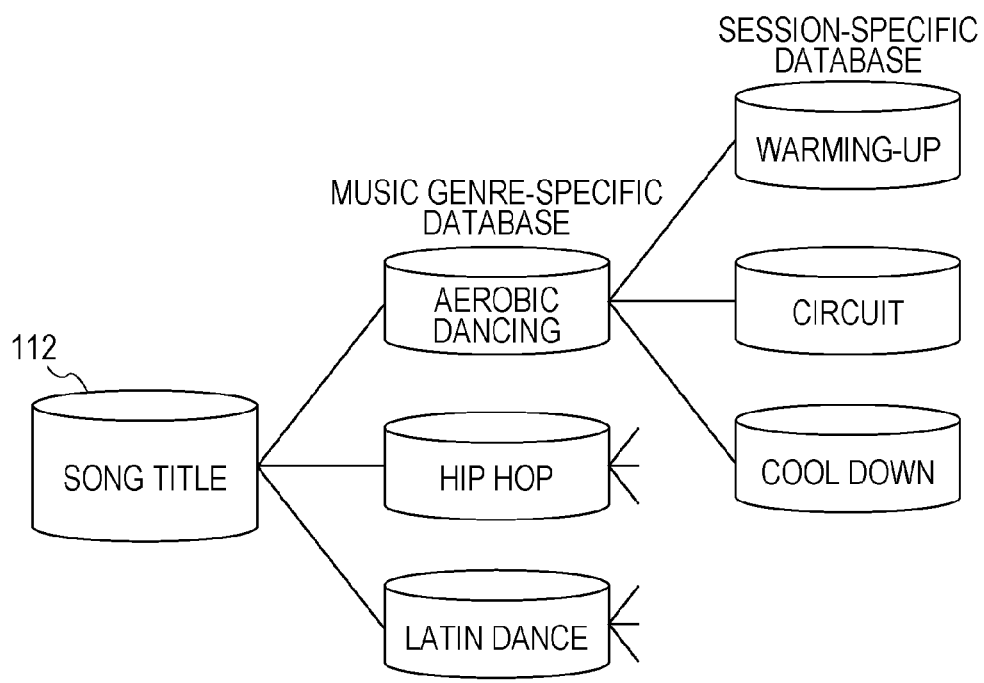
FIG. 7 is a schematic diagram showing the configuration of a song title database.
FIG. 8 is a chart showing an example of a physical-fitness-value determination table.

As shown in FIG. 7, the song title database 112 may store a song title list of songs whose sound can be outputted from the sound output unit 123 in synchronization with presentation of exercise content included in an exercise menu. The song title database 112 may be made up of three kinds of music genre-specific databases "aerobic dancing", "hip hop", and "Latin dance". Each music genre-specific database may be made up of three kinds of session-specific databases "warming-up", "circuit", and "cool down". Each session-specific database may store a song title used in each session.

The physical-fitness-value determination table 105b shown in FIG. 8 may store physical fitness values associated with the ages and exercise habit values of males and the ages and exercise habit values of females, which are included in personal information described later. In the example shown in FIG. 8, 3 is stored as a physical fitness value corresponding to an exercise habit value 3 and an age that fits into a male age range "34-55" indicating an age range from 34 years old to 55 years old. The ratio determination table 105c shown in FIG. 9 stores ratios corresponding to individual user's exercise experience values or physical fitness values described later.

The exercise menu described later may include a plurality of aerobic exercises or anaerobic exercises placed alternately with breaks therebetween. Each ratio stored in the ratio determination table 105c shown in FIG. 9 may indicate the ratio between a break time and an exercise time made up of an aerobic exercise or an anaerobic exercise placed immediately after a break. In the ratio determination table 105c, ratios may be set in advance such that the break time may decrease as the exercise experience value or physical fitness value increases from 1 to 3. Also, in the ratio determination table 105c, ratios may be set in advance such that the exercise time of an exercise presented immediately after a break may increase as the break time decreases. In the example shown in FIG. 9, when the exercise experience value or the physical fitness value is 2, 10/30 may be stored as the ratio between the presentation times of a break and an exercise. The ratio "10/30" indicates that the ratio between a break time and the exercise time of an exercise placed immediately after the corresponding break is 10 to 30.

Personal information may be inputted to the personal information management computer 2 for each user and stored into the personal information database 27. Personal information may be made up of personal identification information, an exercise habit value, age, sex, a normal heart rate, and an exercise experience value. Personal identification information identifies each user. An exercise habit value indicates how much the user is in the habit of doing exercise. An exercise experience value indicates how much experience the user has with each of an aerobic dancing exercise, a hip hop exercise, and a Latin dance exercise. As an exercise habit value, for examples, numbers from 3 to 1 are respectively assigned to the user who exercises daily, the user who exercises weekly, and the user who does not exercise at all. Therefore, a larger exercise habit value indicates a higher frequency with which the user does exercise as a habit.

As an exercise experience value, a number 3 may be assigned if the user has a rich exercise experience with each of an aerobic dancing exercise, a hip hop exercise, and a Latin dance exercise. A number 2 may be assigned if the user has medium exercise experience. A number 1 may be assigned if the user does not have any exercise experience. Therefore, a larger exercise experience value indicates a richer exercise experience the user has. With regard to personal information, a health questionnaire may be displayed on the display unit 23, and the user's answers to the health questionnaire are accepted by the input unit 24. Thus, personal information may be stored and registered into the personal information database 27 of the personal information management computer 2.

The CPU 21 of the personal information management computer 2 reads the user's personal identification information stored in an IC card or the like inserted in the storage medium reading unit 25, and performs authentication. Then, the CPU 21 reads personal information corresponding to the authenticated personal identification information from the personal information database 27. The CPU 21 may specify one of a plurality of exercise support apparatuses 1. The specified exercise support apparatus 1 may be displayed on the display unit 23 and presented to the user, and personal information is given to the specified exercise support apparatus 1 via the communication network N. Next, processing performed in the exercise support apparatus 1 will be described.

The CPU 101 of the exercise support apparatus 1 stores the given personal information into the storage unit 105. The CPU 101 also displays on the first picture display unit 121a a selection screen for accepting selection of training parts and a music genre. In the example shown in FIG. 11, 13 software buttons respectively indicated as "shoulder", "arm", "chest", "back", "abdomen", "flank", "buttock", "inner thigh", "outer thigh", "front thigh", "back thigh", "calf", and "shin" are displayed as training parts together with a message "Select four training parts.". In addition, three software buttons respectively indicated as "aerobic dancing", "hip hop", and "Latin dance" are displayed as music genres together with a message "Select music genre.".

The CPU 101 highlights the software buttons selected by a user's operation accepted by the touch panel unit 122. When four kinds of training parts and one kind of music genre are selected, the CPU 101 may display a software button indicated as "Set" on the selection screen. When a selecting operation on the "Set" icon by the user is detected by the touch panel unit 122, the CPU 101 acquires the selected training parts and music genre. In the example shown in FIG. 11, software buttons indicated as "shoulder", "abdomen", "outer thigh", and "calf" and a software button indicated as "aerobic dancing" are selected and highlighted as the training parts and music genre, respectively, and the "Set" icon may be displayed.

The CPU 101 may select one kind of warming-up exercise content data from the additional exercise database 111*c*, and acquires its content name. The CPU 101 may determine a physical fitness value on the basis of the physical-fitness-value determination table 105*b* stored in the storage unit 105 and the sex, age, and exercise habit value included in the personal information stored in the storage unit 105. Then, the CPU 101 acquires an exercise experience value included in the personal information and corresponding to the selected music genre. Of the music genre-specific databases included in the aerobic exercise database 111*a*, the CPU 101 may make access to a music genre-specific database corresponding to the music genre selected by the user. Further, from the music genre-specific database accessed, the CPU 101 may select the same number of pieces of aerobic exercise content data as the number of the training parts selected on the selection screen, and acquire their respective content names.

In the case when the training parts and music genre may be selected as shown in FIG. 11, the CPU 101 selects four kinds of aerobic exercise content data from the aerobic dancing database included in the aerobic exercise database 111*a*, and acquires their respective content names. From the anaerobic exercise database 111*b*, the CPU 101 may select pieces of anaerobic exercise content data corresponding to the training parts selected by the user and acquires their respective content names. In the case when four kinds of training parts are selected as shown in FIG. 11, the CPU 101 selects four kinds of training-specific anaerobic exercise content data from the anaerobic exercise database 111*b* and acquires their respective content names. From the additional exercise database 111*c*, the CPU 101 may select stretch exercise content data and deep breathing exercise content data and acquires their respective content names. Next, a description will be given of a process in which an exercise menu is generated from a plurality of kinds of content names acquired by the CPU 101.

The CPU 101 may generate an exercise menu by executing an exercise menu generation process described later, and store the generated exercise menu into the storage unit 105. An exercise menu may be made up of six sessions in total including a single warming-up session, four identical circuit sessions, and a single cool down session. In the example of an exercise menu shown in FIG. 12, the exercise menu is made up of a warming-up session having a session name "warming-up", four identical circuit sessions having session names "first circuit" to "fourth circuit", and a cool down session having a session name "cool down".

The warming-up session is made up of the content name "warming-up" of warming-up exercise content data. A single circuit session may be made up of a plurality of aerobic and anaerobic exercises placed alternately with breaks therebetween. In the example of the first circuit session having the session name "first circuit" shown in FIG. 12, the respective content names "aerobic 1" to "aerobic 4" of four kinds of aerobic exercise content data, the respective content names "anaerobic 1" to "anaerobic 4" of four kinds of anaerobic exercises content data, and eight content names "break" indicating a break are placed alternately.

The cool down session may be made up of a content name "stretch" of stretch exercise content data and a content name "deep breathing" of deep breathing exercise content data. The user's exercise experience value with respect to the selected music genre may be read from the personal information stored in the storage unit 105, and a ratio corresponding to the read exercise experience value may be read from the ratio determination table 105*c*. The total time of a break time and the exercise time of an exercise presented immediately after the break, which is set in advance and stored in the storage unit 105, is read. In accordance with the ratio read from the ratio determination table 105*c*, the break time and the exercise time of the exercise placed immediately after the break may be allotted.

In the example of the exercise menu shown in FIG. 12, a total time of 40 seconds, which is the total time of a break and the exercise time of an exercise placed immediately after the break, is read from the storage unit 105. Then, a ratio of 10/30 corresponding to an exercise experience value 2 is read from the ratio determination table 105*c*. Of the total time of 40 seconds, 10 seconds is allotted as a break time to the content name "break" placed immediately before the content name "aerobic 1" or the like indicating an aerobic exercise, in accordance with the ratio of 10/30. Also, 30 seconds is allotted as an exercise time to "aerobic 1" or the like placed immediately after "break". That is, 10 seconds and 30 seconds are respectively allotted as the presentation time of "break" and the presentation of "aerobic 1" or the like.

Next, a ratio corresponding to the user's physical fitness value is read from the ratio determination table 105*c*. In accordance with the ratio read from the ratio determination table 105*c*, the total time is divided up and allotted to each of the break time and the exercise time of an anaerobic exercise placed immediately after the break. In the example of the exercise menu shown in FIG. 12, a ratio of 5/35 corresponding to a physical fitness value 3 is read from the ratio determination table 105*c*. In accordance with the ratio of 5/35, the exercise time for the content name "anaerobic 1" indicating an anaerobic exercise, and the break time for the content name "break" placed immediately before the content name "anaerobic 1" are determined. Of the total time of 40 seconds, the break time of "break" and the exercise time of "anaerobic 1" are determined to be 5 seconds and 35 seconds, respectively. The determined times are allotted as the break time and the exercise time. That is, 5 seconds and 35 seconds are respectively allotted as the presentation time of "break" and the presentation time of "anaerobic 1". In the example of the exercise menu shown in FIG. 12, the presentation time of each circuit session is always 320 seconds.

The respective exercise times of the warming-up exercise, stretch exercise, and deep breathing exercise which are set in advance and stored in the storage unit 105 are read. The presentation times corresponding to the content name "warming-up" and the content names "stretch" and "deep breathing" are set in the exercise menu. The presentation time of each picture or image constituting the exercise menu is always constant irrespective of the exercise experience value and the physical fitness value. In the example of the exercise menu shown in FIG. 12, the presentation time of the warming-up session is a preset time of 300 seconds. Also, the presentation times of the stretch exercise and deep breathing exercise constituting the cool down session are preset times of 50 seconds and 60 seconds, respectively. The presentation time of the four circuit sessions is always constant at 320 seconds as described above. Therefore, the total presentation time of the warming-up session, the cool down session, and the circuit sessions is constant at 1690 seconds.

The CPU 101 selects a single song for each of the warming-up, circuit, and cool down sessions, from a music genre-specific database corresponding to the music genre selected by the user. Each of the selected song titles associated with the session names may be added to the exercise menu. In the example of the exercise menu shown in FIG. 12, "song title 1" and "song title 3" are set in association with the session names "warming-up" and "cool down", respectively. Also, a song title "song title 2" is set in association with the session names "first circuit" to "fourth circuit". The individual content names constituting the exercise menu shown in FIG. 12 are assigned sequence numbers sequentially from the top of the table shown in FIG. 12. The exercise menu with the sequence numbers assigned may be stored into the storage unit 105.

The CPU 101 transmits to the server computer 3 a song data request for requesting the song data of song titles included in the exercise menu stored in the storage unit 105. The CPU 101 receives the song data transmitted from the server computer 3 in response to the song data request. The CPU 101 displays the picture or image of exercise content data on the first picture display unit 121*a* or the second picture display unit 121*b* on the basis of the exercise menu. At the same time, the CPU 101 performs an exercise menu presentation process in which the sound based on sound data included in the song data and the exercise content data is outputted from the sound output units 123. In the picture or image displayed on the first picture display unit 121*a* or the second picture display unit 121*b* by the CPU 101, a computer graphics-generated image of a person mimicking an instructor who instructs the user on exercises is displayed together with the background image.

Figure 13:
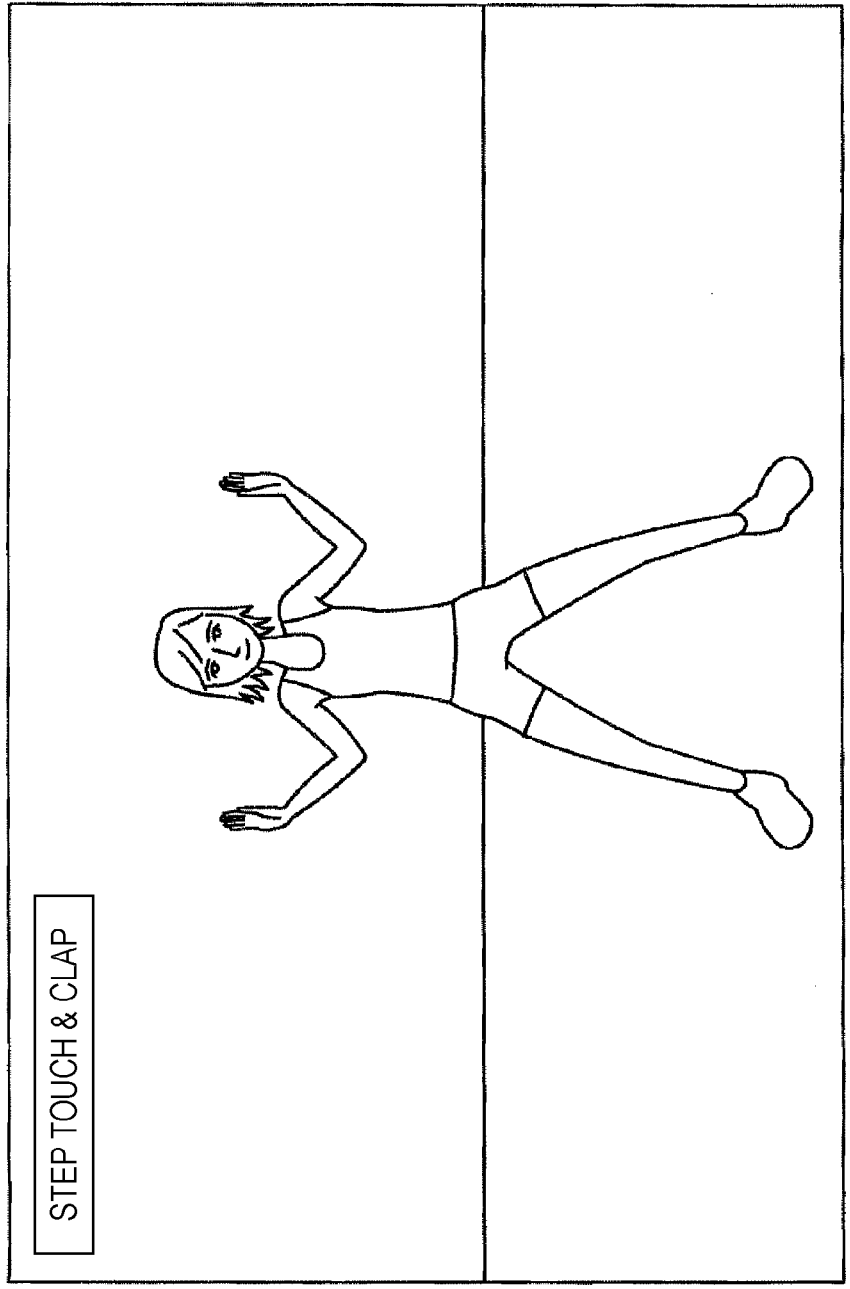
FIG. 13 is a schematic diagram showing an example of a screen presenting an aerobic exercise.

In the example shown in FIG. 13, a person's image instructing an aerobic exercise involving step movements to the left and right while clapping hands may be displayed three-dimensionally together with the background, and also an exercise name "step touch & clap" may be displayed. When a break placed immediately before aerobic exercise content is being presented, a break screen including a scaled-down image or simplified image of the aerobic exercise content to be displayed next, a software bar indicating the remaining time of the break time, and the like may be displayed.

Figure 14:
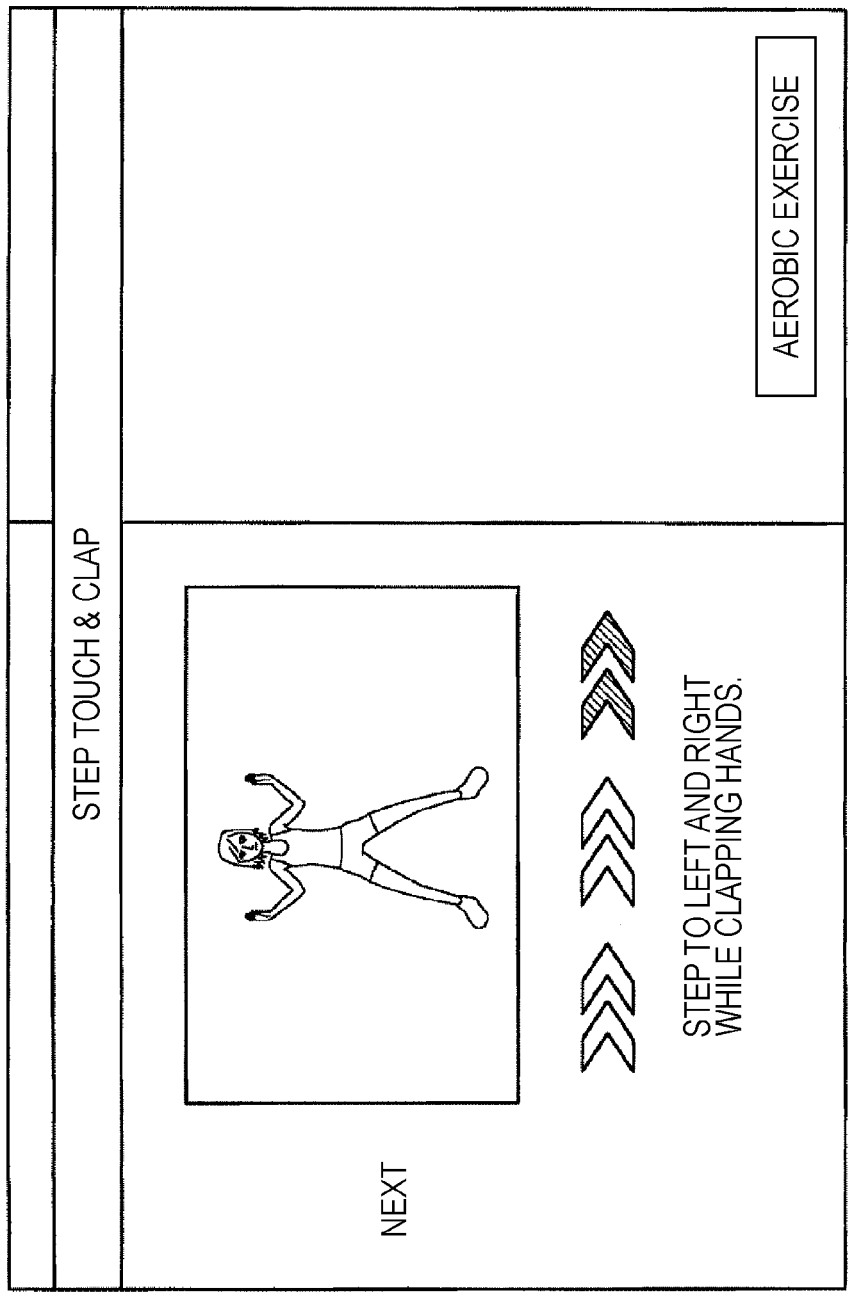
FIG. 14 is a schematic diagram showing an example of a screen presenting a break placed immediately before anaerobic exercise content.

In the example shown in FIG. 14, a scaled-down representation of a three-dimensionally displayed person's image instructing an aerobic exercise, which is the next aerobic exercise content to be presented and involves step movements to the left and right while clapping hands, is displayed together with the background. Also, in FIG. 14, a message "NEXT" indicating that the scaled-down image represents the exercise to be presented next is displayed. A message "aerobic exercise" indicating that the exercise content to be displayed next is one indicative of an aerobic exercise is displayed. The name "step touch & clap" of the exercise that will be displayed next, a message "Step to the left and right while clapping hands." explaining the exercise, and a software bar indicating the remaining time of the break time may be displayed.

Figure 15:
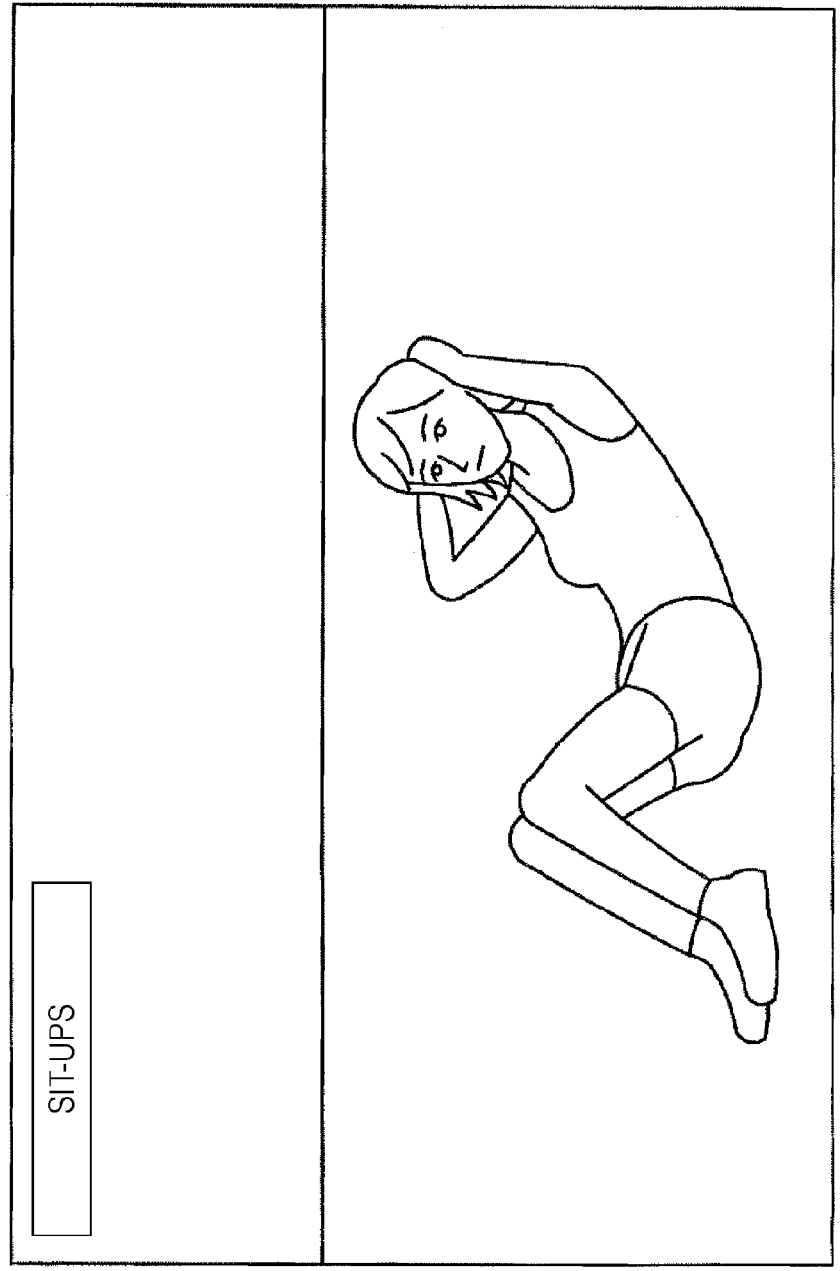
FIG. 15 is a schematic diagram showing an example of a screen presenting an anaerobic exercise.

In the example shown in FIG. 15, a person's image instructing a sit-up exercise which is an anaerobic exercise for training the abdomen may be displayed three-dimensionally together with the background, and a training part "abdominal muscles" may be displayed. When presenting a break placed immediately before anaerobic exercise content, a break screen including a scaled-down screen or simplified screen of the anaerobic exercise content to be displayed next, the training part, a software bar indicating the remaining time of the break time, and the like may be displayed.

Figure 16:
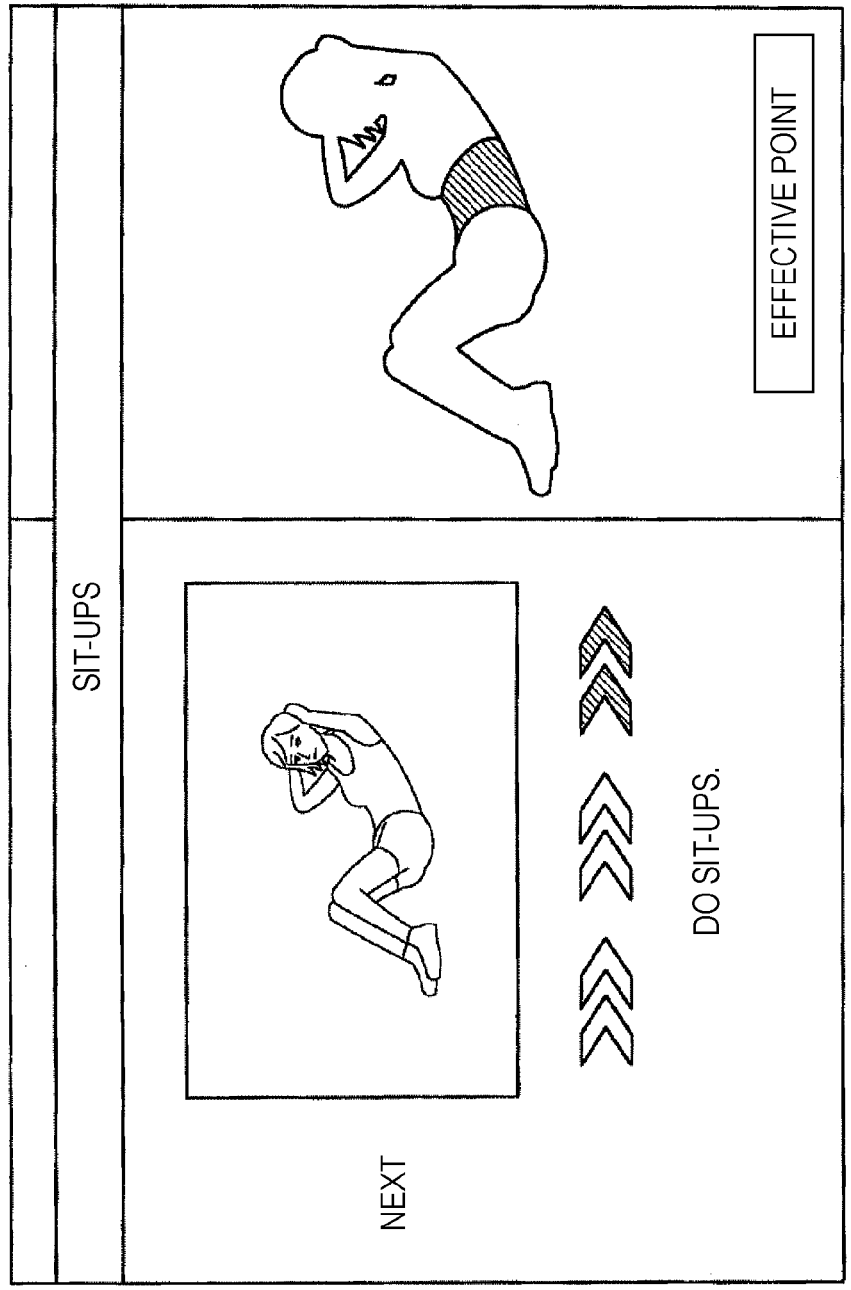
FIG. 16 a schematic diagram showing an example of a screen presenting a break placed immediately before an anaerobic exercise.

In the example shown in FIG. 16, a scaled-down representation of a three-dimensionally displayed person's image, which represents the next anaerobic exercise content to be presented and involves a sit-up exercise, may be displayed together with the background. Also, in FIG. 16, a message "NEXT" indicating that the scaled-down image represents the exercise to be presented next is displayed. A message "effective point" indicating the training part that can be trained with the exercise content that will be displayed next, and the training part indicated by highlighting a part of the person's image may be displayed. The name "sit-ups" of the exercise that will be displayed next, a message "Do sit-ups." explaining the exercise, and a software bar indicating the remaining time of the break time may be displayed.

When presenting each of a break and an aerobic exercise or anaerobic exercise, sound data included in exercise content data may be outputted, and the song data of a song title associated with the content name of the exercise content data being currently displayed is played back. When all the pieces of exercise content data included in the exercise menu have been presented, the exercise menu presentation process is ended, and the song data stored in the storage unit 105 is deleted.

Figure 17:
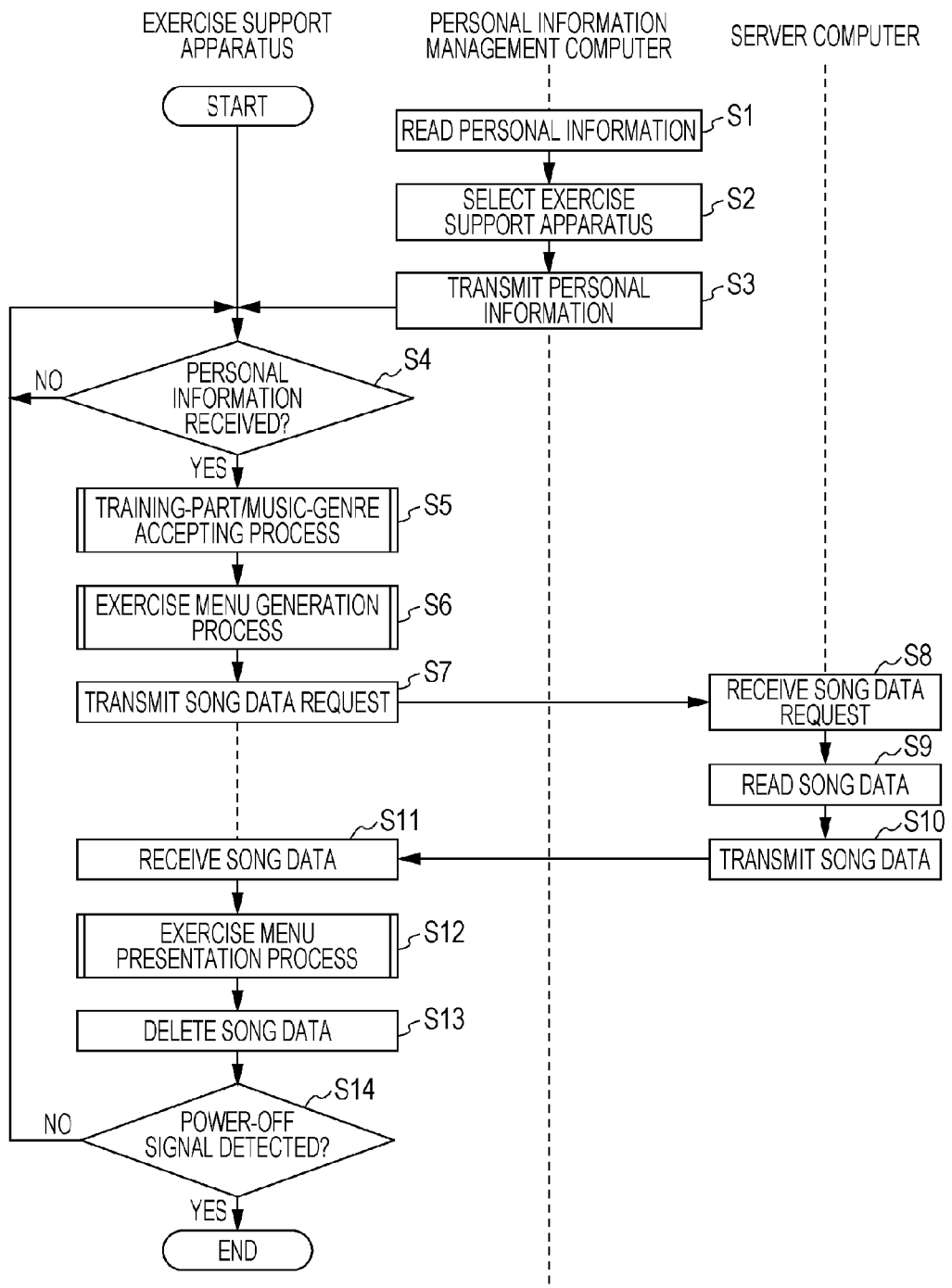
FIG. 17 is a flowchart showing the procedure of processing executed by an exercise support apparatus, a personal information management computer, and a server computer.

The exercise support apparatus 1 starts processing upon detecting a power-on signal outputted upon a connecting operation of a power switch (not shown) provided to the housing 12. Each of the personal information management computer 2 and the server computer 3 starts processing upon accepting an activating operation. As shown in FIG. 17, the CPU 21 of the personal information management computer 2 reads personal information from the personal information database 27 (step S1). The CPU 21 selects one of a plurality of exercise support apparatuses 1 (step S2). The CPU 21 transmits the read personal information to the selected exercise support apparatus 1 (step S3). The CPU 101 of the exercise support apparatus 1 determines whether or not personal information has been received (step S4). If it is determined that personal information has not been received (NO in step S4), the CPU 101 returns the processing to step S4 in which it is determined whether or not personal information has been received.

If it is determined that personal information has been received (YES in step S4), the CPU 101 executes a training-part/music-genre accepting process described later to acquire training parts and a music genre specified by the user (step S5). The CPU 101 executes an exercise menu generation process of generating an exercise menu in accordance with the user's personal information, and the user-specified training parts and music genre (step S6). The CPU 101 transmits to the server computer 3 a song data request requesting for the song data having song titles included in the exercise menu (step S7). The CPU (not shown) of the server computer 3 receives the song data request (step S8).

The CPU of the server computer 3 reads song data from a database (not shown) included in the server computer 3 (step S9). The CPU of the server computer 3 transmits the read song data to the exercise support apparatus 1 (step S10). The CPU 101 of the exercise support apparatus 1 receives the song data given from the server computer 3 and stores the song data into the storage unit 105 (step S11). The CPU 101 executes an exercise menu presentation process of outputting the picture or image and sound based on exercise content and the song data in accordance with the exercise menu (step S12). The CPU 101 deletes the song data stored in the storage unit 105 (step S13).

The CPU 101 determines whether or not a power-off signal outputted upon a disconnecting operation of the power switch (not shown) provided to the housing 12 has been detected (step S14). If it is determined that the power-off signal has not been detected (NO in step S14), the CPU 101 returns the processing to step S4 in which it is determined whether or not personal information has been received. If it is determined that the power-off signal has been detected (YES in step S14), the CPU 101 ends the processing that is being executed in the exercise support apparatus 1. Each of the personal information management computer 2 and the server computer 3 is adapted to end processing upon accepting a shut-down operation.

Figure 18:
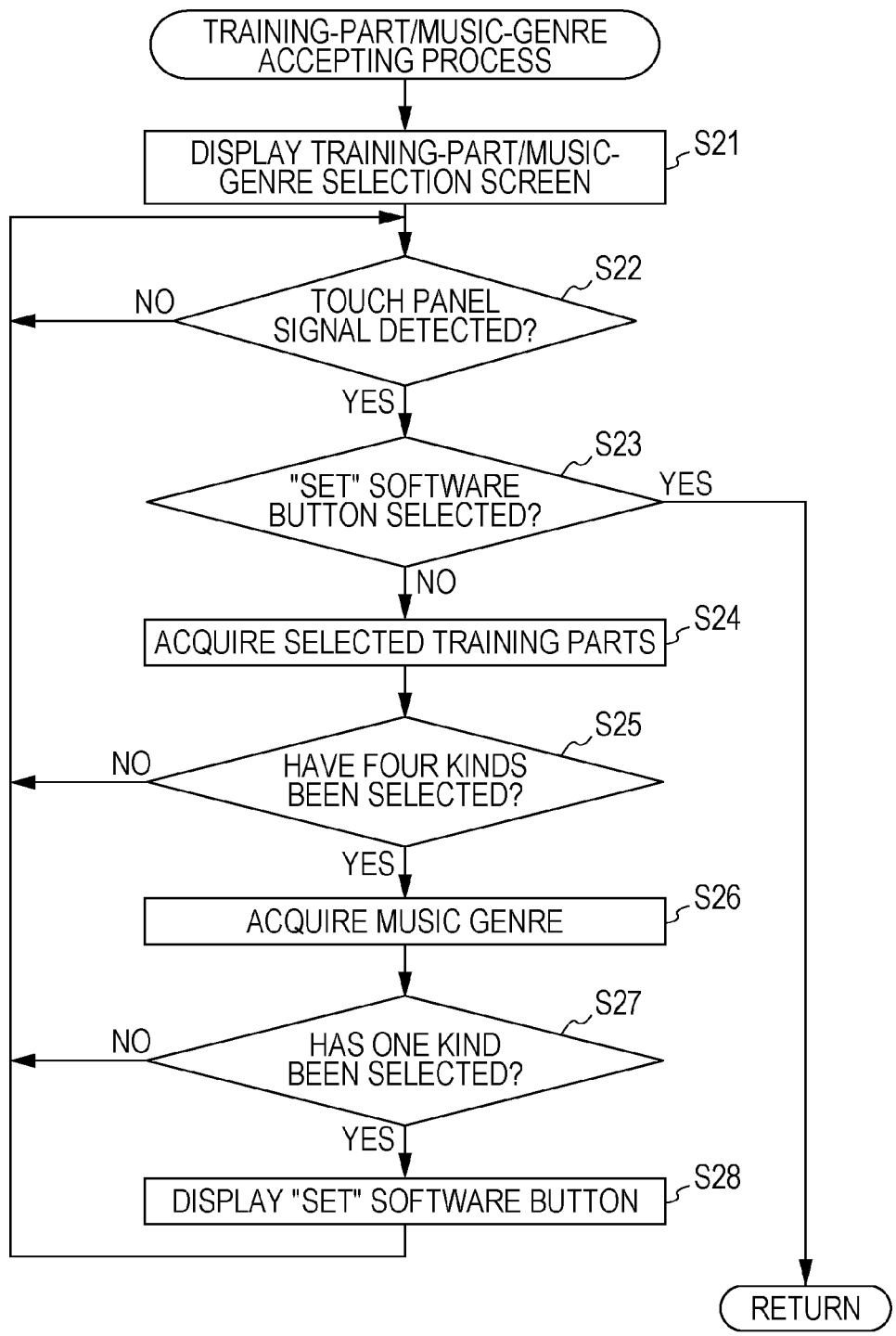
FIG. 18 is a flowchart showing the procedure of a training-part/music-genre accepting process.

FIG. 18 shows the steps involved in the training-part/music-genre accepting process of step S5. The CPU 101 of the exercise support apparatus 1 displays, on the first picture display unit 121a, a training-part/music-genre selection screen on which the "Set" software button is not displayed (step S21). The CPU 101 determines whether or not a touch panel signal inputted to the touch panel signal input unit 107 from the touch panel unit 122 has been detected (step S22). If it is determined that a touch panel signal has not been detected (NO in step S22), the CPU 101 returns the processing to step S22 in which it is determined whether or not a touch panel signal has been detected. If it is determined that a touch panel signal has been detected (YES in step S22), the CPU 101 determines whether or not the "Set" software button displayed on the selection screen has been selected, from position information indicated by the detected touch panel signal (step S23).

If it is determined that the "Set" software button has been selected (YES in step S23), the CPU 101 ends the training-part/music-genre accepting process. If it is determined that the "Set" software button has not been selected (NO in step S23), the CPU 101 acquires the training parts being selected on the selection screen (step S24). The CPU 101 determines whether or not four kinds of training parts have been selected (step S25). If it is determined that four kinds of training parts have not been selected (NO in step S25), the CPU 101 returns the processing to step S22 in which it is determined whether or not a touch panel signal has been detected.

If it is determined that four kinds of training parts have been selected (YES in step S25), the CPU 101 acquires the music genre being selected on the selection screen (step S26). The CPU 101 determines whether or not one kind of music genre has been selected (step S27). If it is determined that one kind of music genre has not been selected (NO in step S27), the CPU 101 returns the processing to step S22 in which it is determined whether or not a touch panel signal has been detected. If it is determined that one kind of music genre has been selected (YES in step S27), the CPU 101 displays the "Set" software button on the selection screen (step S28), and returns the processing to step S22 in which it is determined whether or not a touch panel signal has been detected.

Figure 19:
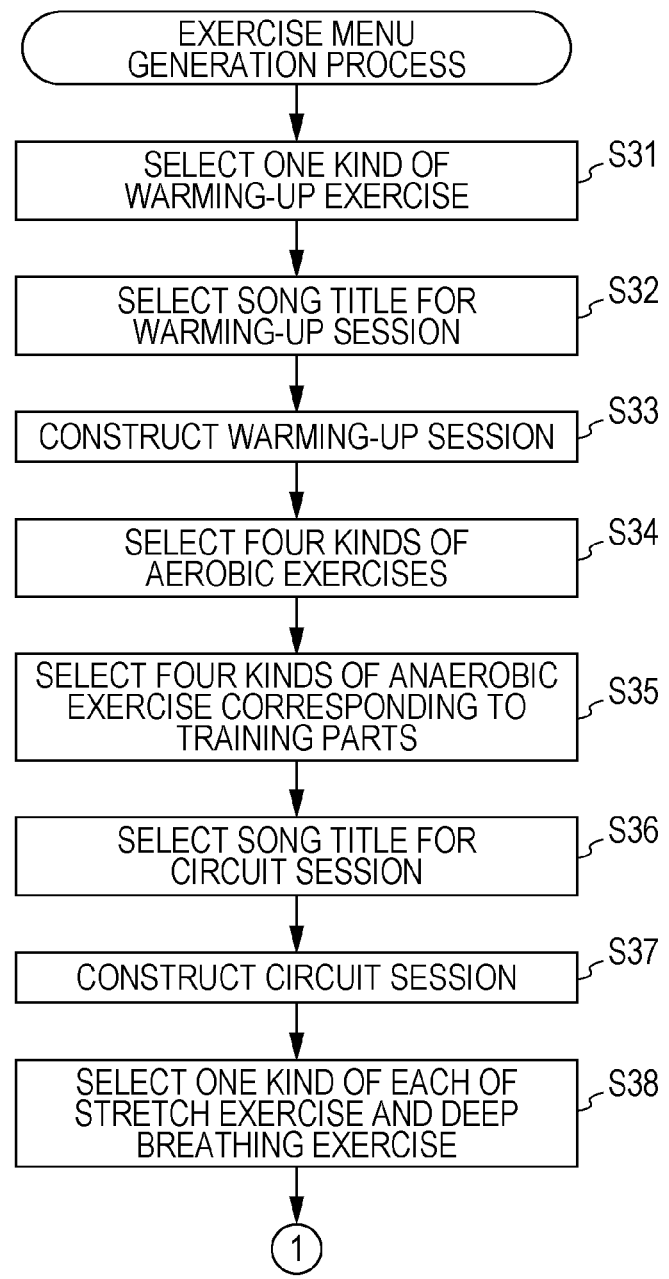
FIG. 19 is a flowchart showing the procedure of an exercise menu generation process.
Figure 20:
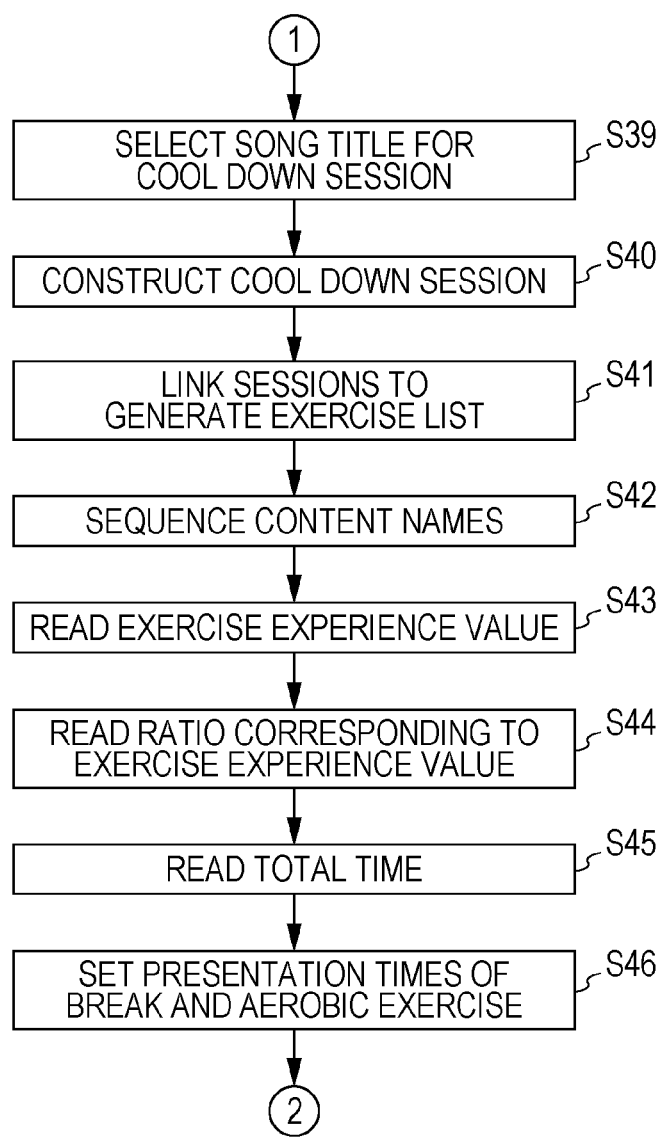
FIG. 20 is a flowchart showing the procedure of an exercise menu generation process continued from FIG. 19.
Figure 21:
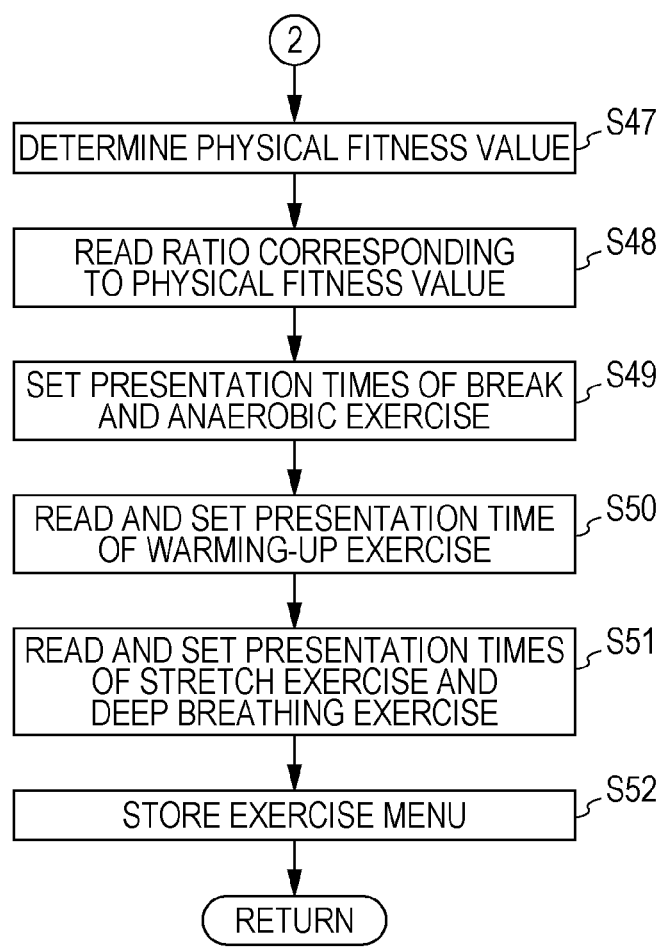
FIG. 21 is a flowchart showing the procedure of an exercise menu generation process continued from FIG. 20.

FIGS. 19-21 show the steps involved in the exercise menu generation process of step S108. The CPU 101 of the exercise support apparatus 1 selects one kind of warming-up exercise content data from the additional exercise database 111c and acquires its content name (step S31). The CPU 101 selects a song title for warming-up session from the song title database 112 (step S32). The CPU 101 constructs a warming-up session from the content name of warming-up exercise content and the song title for warming-up session (step S33). The CPU 101 selects four kinds of aerobic exercise content data from the aerobic exercise database 111a, and acquires their respective content names (step S34).

The CPU 101 selects four kinds of anaerobic exercises respectively corresponding to the selected training parts, and acquires their respective content names (step S35). The CPU 101 selects a song title for circuit session from the song title database 112 (step S36). The CPU 101 constructs a circuit session from the respective content names of aerobic exercise content and anaerobic exercise content, and the song title for circuit session (step S37). The CPU 101 selects one kind of each of stretch exercise content data and deep breathing content data from the additional exercise database 111c, and acquires their respective content names (step S38). The CPU 101 selects a song title for cool down session from the song title database 112 (step S39).

The CPU 101 constructs a cool down session from the respective content names of stretch exercise content and deep breathing exercise content, and the song title for cool down session (step S40). The CPU 101 generates an exercise list by linking the respective sessions in the order of the warming-up session, the four identical circuit sessions, and the cool down session (step S41). The CPU 101 sequences the content names included in the exercise list from the top (step S42). The CPU 101 reads an exercise experience value associated with the selected music genre, from personal information given from the personal information management computer 2 and stored into the storage unit 105 (step S43).

The CPU 101 reads a ratio corresponding to the read exercise experience value from the ratio determination table 105c (step S44). The CPU 101 reads the total time of a break time and the exercise time of an exercise presented immediately after the break, which is set in advance and stored in the storage unit 105 (step S45). In accordance with the ratio corresponding to the exercise experience value, the CPU 101 sets the break time and the exercise time of an aerobic exercise placed immediately after the break, that is, the respective presentation times of the break and the aerobic exercise placed immediately after the break (step S46).

The CPU 101 determines a physical fitness value on the basis of the age, sex, exercise habit value, and exercise experience value included in the personal information, and the physical-fitness-value determination table 105b stored in the storage unit 105 (step S47). The CPU 101 reads a ratio corresponding to the determined physical fitness value from the ratio determination table 105c (step S48). In accordance with the ratio corresponding to the physical fitness value, the CPU 101 sets the break time and the exercise time of an anaerobic exercise placed immediately after the break, that is, the respective presentation times of the break and the anaerobic exercise placed immediately after the break (step S49).

The CPU 101 reads and sets the exercise time, that is, presentation time for a warming-up exercise, which is determined in advance and stored in the storage unit 105 (step S50). The CPU 101 reads and sets each of the exercise times, that is, presentation times for a stretch exercise and a deep breathing exercise, which are determined in advance and stored in the storage unit 105 (step S51). The CPU 101 stores an exercise list in which individual content names are sequenced and their respective presentation times are set, into the storage unit 105 as an exercise menu (step S52), and ends the exercise menu generation process.

Figure 22:
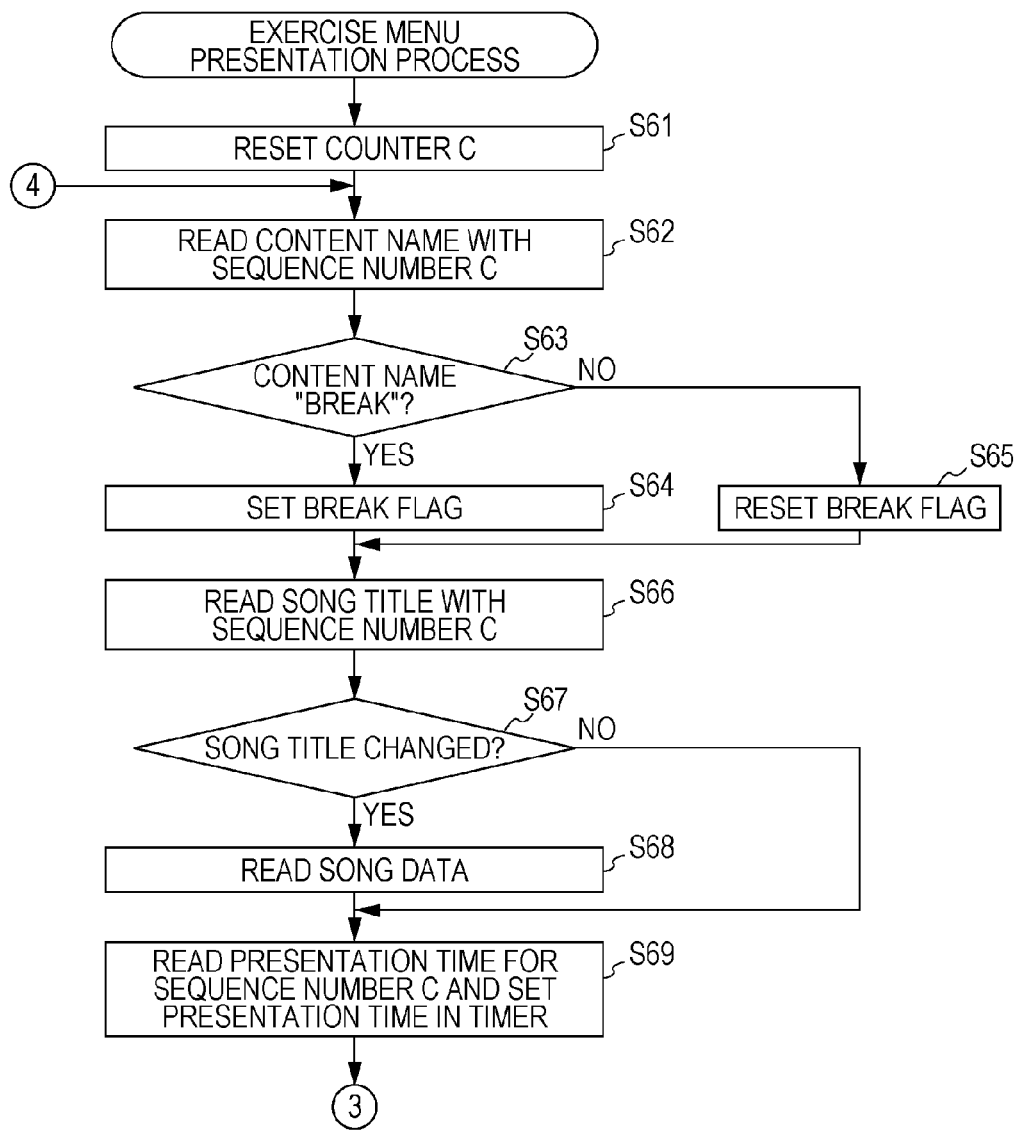
FIG. 22 is a flowchart showing the procedure of an exercise menu presentation process.

FIGS. 22 and 23 show the steps involved in the exercise menu presentation process of step S12. The CPU 101 resets a counter C stored in the RAM 102 (step S61). The CPU 101 reads a content name with a sequence number indicated by the counter C, that is, a sequence number C from the exercise menu stored in the storage unit 105 (step S62). The CPU 101 determines whether or not the read content name is "break" (step S63). If it is determined that the read content name is "break" (YES in step S63), the CPU 101 sets a break flag stored in the RAM 102 (step S64), and reads the song title with the sequence number C from the exercise menu (step S66). If it is determined that the read content name is not "break" (NO in step S63), the CPU 101 resets the break flag stored in the RAM 102 (step S65), and returns the processing to step S66 in which the song title with the sequence number C is read from the exercise menu.

The CPU 101 determines whether or not the read song title has been changed from an already read song title (step S67).

If it is determined that the song title has been changed (YES in step S67), the CPU 101 reads the song data indicative of the newly read song title from the storage unit 105 (step S68). The CPU 101 reads the presentation time for the sequence number C from the exercise menu, and sets the presentation time in the timer 113 (step S69). If it is determined that the song title has not been changed (NO in step S67) in step S67 in which it is determined whether or not the read song title has been changed from an already read song title, the CPU 101 returns the processing to step S69 in which the presentation time for the sequence number C is read from the exercise menu and set in the timer 113.

The CPU 101 determines whether or not the break flag stored in the RAM 102 is set (step S70). If it is determined that the break flag is set (YES in step S70), the CPU 101 reads a content name with a sequence number "C+1" from the exercise menu (step S71). The CPU 101 reads exercise content data having the read content name from the exercise content database 111 (step S72). The CPU 101 starts outputting of the playback sound of song data, and starts outputting of a break screen including a simplified screen of exercise content data, a software bar indicating the remaining time, and the like (step S73). The CPU 101 starts the timing by the timer 113 (step S76).

If it is determined that the break flag is not set (NO in step S70) in step S70 in which it is determined whether or not the break flag stored in the RAM 102 is set, the CPU 101 reads exercise content data having the read content name from the exercise content database 111 (step S74). The CPU 101 starts outputting of the playback sound of song data, and also starts outputting of the picture or image and sound of exercise content data in synchronization with the playback sound (step S75). The CPU 101 returns the processing to step S76 in which timing by the timer 113 is started. The CPU 101 determines whether or not a timer interrupt signal, which is outputted by the timer 113 upon elapse of a set presentation time, has been detected (step S77).

If it is determined that a timer interrupt signal has not been detected (NO in step S77), the CPU 101 returns the processing to step S77 in which it is determined whether or not a timer interrupt signal has been detected. If it is determined that a timer interrupt signal has been detected (YES in step S77), the CPU 101 increments the counter C (step S78). The CPU 101 determines whether or not the counter C exceeds the total number of pieces of exercise content included in the exercise menu (step S79). If it is determined that the total number is not exceeded (NO in step S79), the CPU 101 returns the processing to step S62 in which the content name of the sequence number C is read from the exercise menu. If it is determined that the total number is exceeded (YES in step S79), the CPU 101 ends the exercise menu presentation process.

While the above description is directed to the case in which each of an aerobic exercise and an anaerobic exercise is placed after a break in the exercise menu, this should not be construed restrictively. Each break may be placed after an aerobic exercise and an anaerobic exercise. In this case, the respective presentation times of an aerobic exercise and a break placed immediately after the aerobic exercise may be preferably set in accordance with a ratio corresponding to an exercise experience value, and the respective presentation times of an anaerobic exercise and a break placed immediately after the anaerobic exercise may be preferably set in accordance with a ratio corresponding to a physical fitness value.

In the example of an exercise menu shown in FIG. 24, of the total time of 40 seconds, 30 seconds and 10 seconds are respectively allotted and set as presentation times associated with a content name "aerobic 1" indicating an aerobic exercise, and a content name "break" placed immediately after the aerobic exercise, in accordance with a ratio of 10/30 read on the basis of an exercise experience value. Also, of the total time of 40 seconds, 35 seconds and 5 seconds are respectively allotted and set as presentation times associated with a content name "anaerobic 1" indicating an anaerobic exercise, and a content name "break" placed immediately after the anaerobic exercise, in accordance with a ratio of 5/35 read on the basis of a physical fitness value.

Further, in the case of the circuit session having a circuit name "first circuit" shown in FIG. 24, a break is placed after a content name "aerobic 1". In this case, a scaled-down image of the aerobic exercise "aerobic 1" to be displayed thereafter may be presented in the warming-up session, or a content name "break" may be inserted immediately before the content name "aerobic 1" in the first circuit session and a scaled-down image of the content name "aerobic 1" may be presented. Also, as the content name "break" placed at the end of the fourth circuit session, a scaled-down screen of the stretch exercise included in the cool down session which is placed next may be displayed, or such a break may be omitted.

While Embodiment 1 is directed to the case in which one kind of each of warming-up exercise content, stretch exercise content, and deep breathing exercise content may be stored in the additional exercise database 111c, this should not be construed restrictively. A plurality of kinds of each of these exercise contents may be stored, and a plurality of contents may be selected from each of these to construct a warming-up session and a cool down session.

While the above description is directed to the case in which the exercise experience value and the physical fitness value are classified into three levels, this should not be constructed restrictively. It suffices that the ratio determination table 105c be constructed in accordance with the number of levels. Also, while the above description is directed to the case in which the song title database 112 includes three kinds of music genre-specific databases, this should not be constructed restrictively. The song title database 112 may have less than three kinds or four or more kinds of music genre-specific databases, or may include a plurality of kinds of singer-specific databases. In addition, while the above description is directed to the case in which the ratios of the exercise times of the aerobic exercise and anaerobic exercises to the break time are set on the basis of the exercise experience value and the physical fitness value, the kind of each aerobic exercise and anaerobic exercise may be also selected on the basis of the exercise experience value and the physical fitness value.

While the above description is directed to the case in which 13 kinds of parts are provided as training parts, this should not be constructed restrictively. As training parts, 12 kinds or less, or 14 kinds of more of parts may be provided. In this case, the anaerobic exercise database 111b is configured to include anaerobic exercise content data according to the number of kinds of parts. Also, while the above description is directed to the case in which the control computer 10 includes the exercise content database 111, this should not be constructed restrictively. The exercise content database 111 may be an externally provided exercise content database that is mutually connected to the control computer 10 via the communication network N or the like so as to transmit exercise content data upon request from the control computer 10.

While the above description is directed to the case in which the total presentation time of an exercise menu is 1690 seconds, this should not be construed restrictively. The storage unit 105 may be so configured that the presentation time of a warming-up, the total of the presentation times of breaks and exercises placed immediately after the breaks, the presentation time of a stretch exercise, and the presentation time of a deep breathing exercise respectively corresponding to a plurality of presentation times in the exercise menu are set in advance and stored in the storage unit 105. One of the plurality of presentation times in the exercise menu may be made selectable by the user. Also, while the above description is directed to the case of generating a circuit exercise menu in which aerobic and anaerobic exercises are placed alternately with breaks therebetween, this should not be construed restrictively. It is also possible to generate an exercise menu in which only a plurality of aerobic or anaerobic exercises are placed alternately with no breaks therebetween.

Embodiment 2

Figure 25:
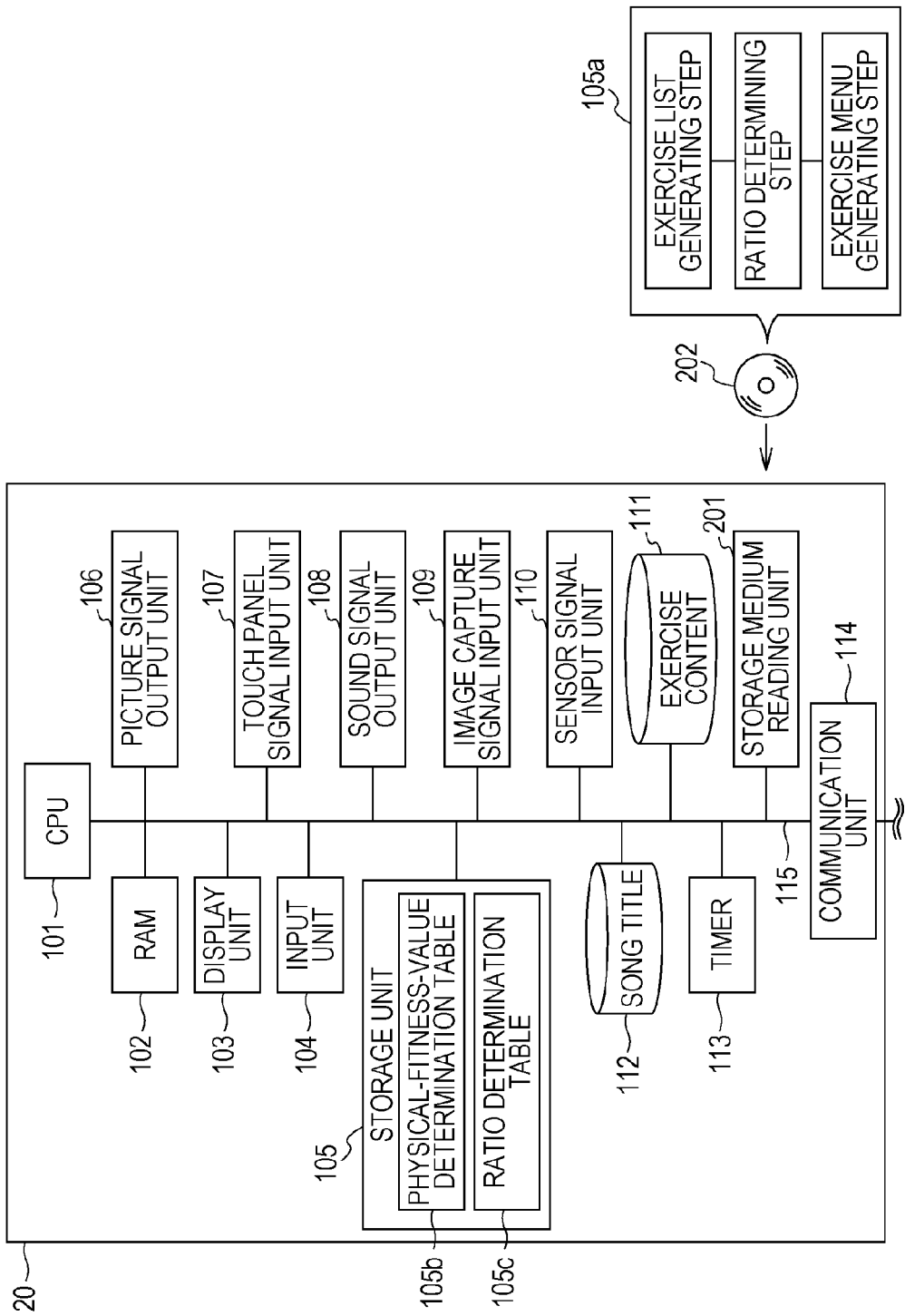
FIG. 25 is a block diagram showing the internal configuration of an exercise support apparatus according to Embodiment 2.

As shown in FIG. 25, in Embodiment 2, the control computer 10 according to Embodiment 1 may be replaced with another example of a control computer which includes a storage medium reading unit. In the drawing, reference numeral 20 denotes a control computer including a storage medium reading unit 201. The control computer 20 is configured to control the exercise support apparatus 1. The storage medium reading unit 201 is connected to the CPU 101 via the bus 115. The control program 105a is recorded on a storage medium 202 that is inserted into the storage medium reading unit 201. The control program 105a is stored into the storage unit 105 via the storage medium reading unit 201 from the storage medium 202.

The CPU 101 executes an exercise list generating step, a ratio determining step, and an exercise menu generating step, in accordance with the control program 105a read into the RAM 102 from the storage unit 105. The exercise list generating step may generate an exercise list including a circuit session made up of aerobic and aerobic exercises, and a break time. The ratio determining step may determine the ratios of the respective exercise times of the aerobic and anaerobic exercises to the break time on the basis of the exercise experience and physical fitness value of the user. The exercise menu generating step may generate an exercise menu by setting the break time and the respective exercise times of the aerobic and anaerobic exercises in the exercise list in accordance with the determined ratios.

The control program 105a according to the present invention may not necessarily be stored in the storage medium 202 such as a CD-ROM or a DVD-ROM, but may be stored in an external memory such as a memory card. In this case, the control program 105a is read from the external memory (not shown) connected to the CPU 101 and is stored into the storage unit 105. Further, such a program may be downloaded to the storage unit 105 by establishing communication between the communication unit 114 and an external computer.

Embodiment 2 is configured as described above. Since the configuration, operation, and processing according to Embodiment 2 are otherwise the same as those in Embodiment 1, the corresponding portions are denoted by the same reference numerals and process names, and detailed description thereof is omitted.

Embodiment 3

Embodiment 3 is configured to generate an exercise menu by a server apparatus and transmit the generated exercise menu to a terminal apparatus, as opposed to Embodiment 1 which is configured to generate an exercise menu by the exercise support apparatus 1. An exercise support system may be made up of the server computer 3 as the server apparatus, and the exercise support apparatus 1 as the terminal apparatus. In Embodiment 3, the storage unit 105 and the exercise content database 111 included in the control computer 1 of the exercise support apparatus 1 according to Embodiment 1 are included in the server computer 3 instead of the control computer 10. The control computer 10 is configured to transmit personal information transmitted from the personal information management computer 2, and acquired training parts and music genre to the server computer 3.

The server computer 3 generates an exercise menu in accordance with a control program read from the storage unit, on the basis of the personal information, the training parts, and the music genre which are transmitted from the control computer 10 of the exercise support apparatus 1. The server computer 3 is configured to transmit the generated exercise menu to the control computer 10 of the exercise support apparatus 1 together with song data and exercise content specified in the exercise menu. The exercise support apparatus 1 is configured to present the exercise content and the song data transmitted from the server computer 3 in accordance with the exercise menu.

Figure 26:
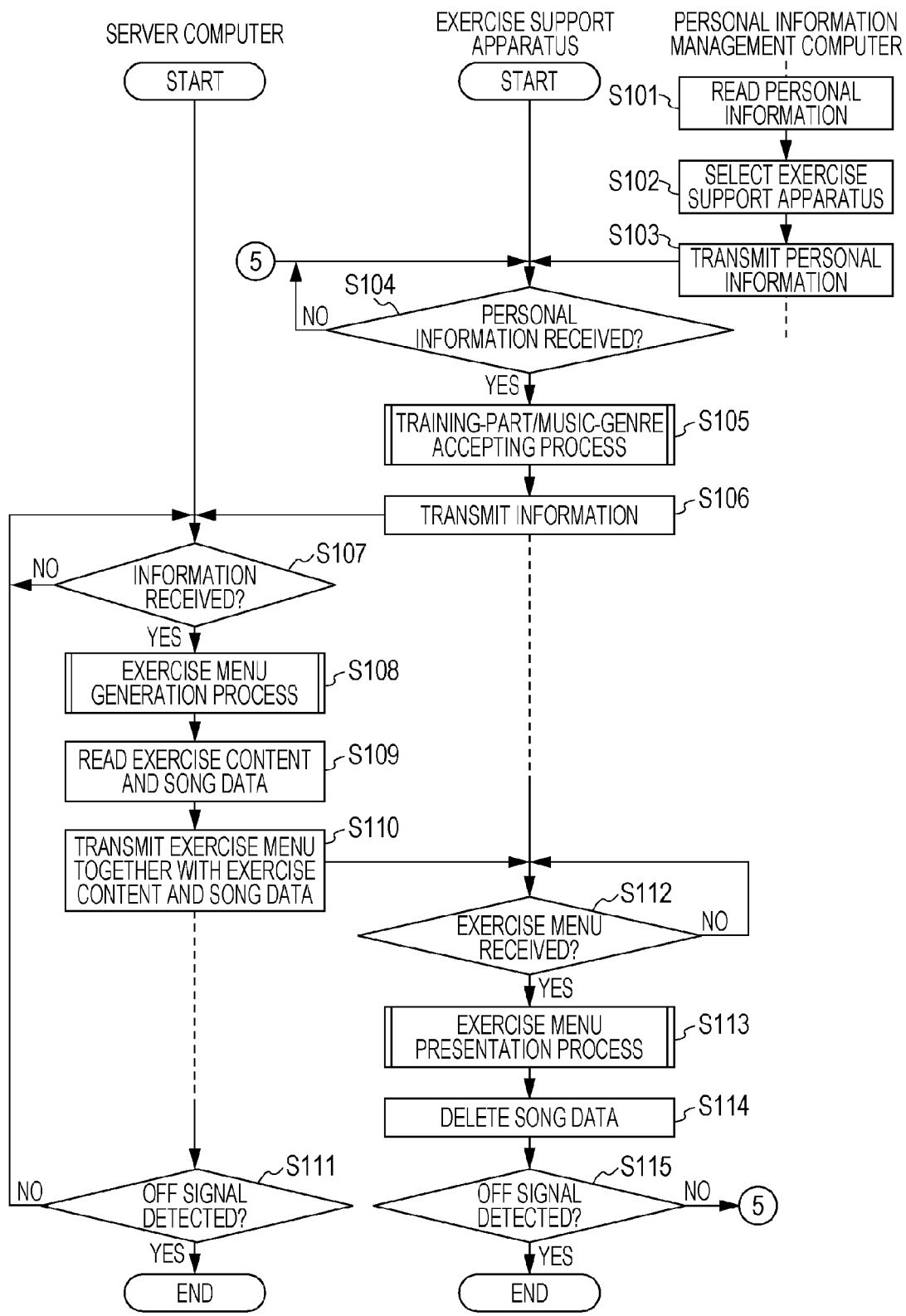
FIG. 26 is a flowchart showing the procedure of processing executed by an exercise support system according to Embodiment 3.

As shown in FIG. 26, the exercise support apparatus 1 starts processing upon detecting a power-on signal outputted upon a connecting operation of a power switch (not shown). Each of the personal information management computer 2 and the server computer 3 starts processing upon accepting an activating operation. The CPU 21 of the personal information management computer 2 reads personal information from the personal information database 27 (step S101). The CPU 21 selects one of a plurality of exercise support apparatuses 1 (step S102). The CPU 21 transmits the read personal information to the selected exercise support apparatus 1 (step S103). The CPU 101 of the exercise support apparatus 1 determines whether or not personal information has been received (step S104). If it is determined that personal information has not been received (NO in step S104), the CPU 101 waits on standby until personal information is received.

If it is determined that personal information has been received (YES in step S104), the CPU 101 executes a training-part/music-genre accepting process (step S105). The CPU 101 transmits information including the personal information, the training parts, and the music genre to the server computer 3 (step S106). A CPU (not shown) of the server computer 3 determines whether or not the information transmitted from the exercise support apparatus 1 has been received (step S107). If it is determined that the information has not been received (NO in step S107), the CPU of the server computer 3 waits on standby until the information is received. If it is determined that the information has been received (YES in step S107), the CPU of the server computer 3 executes an exercise menu generation process (step S108).

The CPU of the server computer 3 reads exercise content data included in an exercise menu and song data indicative of song titles included in the exercise menu, respectively from the exercise content data and the song database (step S109). The CPU of the server computer 3 transmits the exercise menu to the exercise support apparatus 1 together with the exercise content data and the song data (step S110). The CPU 101 of the exercise support apparatus 1 determines whether or not the exercise menu has been received (step S112). If it is determined that the exercise menu has not been received (NO in step S112), the CPU 101 waits on standby until the exercise menu 1 is received. If it is determined that the exercise menu has been received (YES in step S112), the CPU 101 executes an exercise menu presentation process of outputting the picture or image and sound based on the exercise content data and the song data in accordance with the exercise menu (step S113).

The CPU 101 deletes the song data that has been received and stored (step S114). The CPU 101 determines whether or not an off signal outputted upon a disconnecting operation of the power switch (not shown) has been detected (step S115). If it is determined that the off signal has not been detected (NO in step S115), the CPU 101 returns the processing to step S104 in which it is determined whether or not personal information has been received. If it is determined that the off signal has been detected (YES in step S115), the CPU 101 ends processing. The CPU of the server computer 3 determines whether or not an off signal outputted upon accepting a shut-down instruction has been detected (step S111). If it is determined that the off signal has not been detected (NO in step S111), the CPU of the server computer 3 returns the processing to step S107 in which it is determined whether or not information has been received. If it is determined that the off signal has been detected (YES in step S111), the CPU of the server computer 3 ends processing. The personal information management computer 2 is configured to end processing upon accepting a shut-down operation.

While Embodiment 3 is directed to the case in which the physical-fitness-value determination table 105c and the ratio determination table 105c are stored in the storage unit provided in the server computer 3, this should not be constructed restrictively. The physical-fitness-value determination table 105c and the ratio determination table 105c may be stored in the storage unit 105 provided in the control computer 10 of the exercise support apparatus 1. In this case, the control computer 10 may determine a ratio corresponding to each of an exercise experience value and a physical fitness value on the basis of personal information, and transmit the ratio to the server computer 3 instead of the personal information. In the exercise menu generation process, the server computer 3 performs neither determination of an exercise experience value and a physical fitness value, nor reading of a ratio corresponding to each of the exercise experience value and the physical fitness value. Then, the server computer 3 may generate an exercise menu by using the ratio corresponding to each of the exercise experience value and the physical fitness value given from the exercise support apparatus 1.

While the above description is directed to the case in which exercise content data is read from the exercise content database included in the server computer 3, this should not be construed restrictively. The exercise content data may be read from the exercise content database 111 included in the control computer 10 of the exercise support apparatus 1. In this case, the server computer 3 transmits a generated exercise menu to the control computer 10 of the exercise support apparatus 1 together with song data specified in the exercise menu. The control computer 10 sequentially may read exercise content data included in the exercise menu from the exercise content database 111 in accordance with the exercise menu, and outputs the picture or image and sound based on the exercise content data and song data.

While the above description is directed to the case in which the exercise support apparatus 1 performs presentation in accordance with an exercise menu after completing reception of exercise content data and song data transmitted from the server computer 3, this should not be construed restrictively. The server computer 3 may perform streaming distribution of exercise content data and song data to the exercise support apparatus 1 in accordance with an exercise menu. In this case, the exercise support apparatus 1 receives the exercise content data and the song data transmitted from the server computer 3, and performs streaming playback.

Embodiment 3 is configured as described above. Since the configuration, operation, and processing according to Embodiment 3 are otherwise the same as those in Embodiment 1 and Embodiment 2, the corresponding portions are denoted by the same reference numerals and process names, and detailed description thereof is omitted.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. An exercise support apparatus comprising:
    storing unit for storing a plurality of kinds of exercises which includes at least one of an aerobic exercise and at least one of an anaerobic exercise; and
    a processor configured to cause a computer to provide the following functions:
        acquiring first information representative of at least one of an exercise experience and physical fitness of a user;
        selecting a plurality of exercises which includes a plurality of the aerobic exercises and a plurality of the anaerobic exercises stored in the storing unit, and a plurality of breaks;
        generating a circuit exercise menu, including the plurality of selected exercises and the plurality of breaks;
        determining a ratio between each of break times of the breaks included in the exercise menu, and each of exercise times of the aerobic exercises and the anaerobic exercises relative to the breaks, on the basis of the first information;
        determining the ratio between the aerobic exercise time of the plurality of selected aerobic exercises, and the break time of at least one of the plurality of breaks, on the basis of the acquired exercise experience information;
        determining the ratio between the anaerobic exercise time of the plurality of selected anaerobic exercises, and the break time of at least one of plurality of breaks, on the basis of the acquired physical fitness information; and
        generating the circuit exercise menu based on the plurality of selected exercises, the plurality of breaks and the determined ratios.

2. The exercise support apparatus according to claim 1, wherein the processor further causes the computer to provide the functions:
    presenting an image representative of the plurality of aerobic exercises, the plurality of anaerobic exercises and the plurality of breaks included in the exercise menu,
    wherein while presenting an image representative of each one of the breaks included in the exercise menu, presenting the image representative of each break, and the image indicative of one of the anaerobic exercises or the aerobic exercises placed immediately after each break.

3. The exercise support apparatus according to claim 2, wherein:
    the storing unit stores exercise parts respectively indicative of the plurality of kinds of anaerobic exercises; and
    if an aerobic exercise is placed immediately after a break in the exercise menu, displaying an exercise part representative of an anaerobic exercise.

4. The exercise support apparatus according to claim 2, wherein while presenting the image representative of one of the breaks, the presenting unit displays a remaining period of a presentation period of the image representative of at least one break.

5. The exercise support apparatus according to claim 2, further comprising presenting song data which is synchronized with at least one of rhythm and tempo of exercise.

6. The exercise support apparatus according to claim 2, further comprising presenting a 3-dimensional image of an instructor doing exercise according to the exercise menu as the image.

7. The exercise support apparatus according to claim 2, further comprising presenting a scaled down image which represents the aerobic exercise and the anaerobic exercise to be presented next time according to the exercise menu during a break time.

8. The exercise support apparatus according to claim 2, further comprising:
 a receiver for receiving the first information representative of an exercise experience and physical fitness from a terminal apparatus;
 a transmitter for transmitting the ratio determined by the exercise ratio determining unit, and the exercise menu generated by the exercise menu generating unit to the terminal apparatus.

9. A non-transitory computer readable storage medium recording a program to be executed by the computer, the program causing a computer to perform steps comprising:
 acquiring first information representative of at least one of an exercise experience and physical fitness of a user;
 storing a plurality of kinds of exercises which includes at least one of an aerobic exercise and at least one of an anaerobic exercise;
 selecting a plurality of exercises which includes a plurality of aerobic exercises and a plurality of the anaerobic exercises stored in the storing unit, and a plurality of breaks;
 generating an exercise menu, including the plurality of selected exercises and the plurality of breaks; and
 determining a ratio between each of break times of the breaks included in the exercise menu, and each of exercise times of the aerobic exercises and the anaerobic exercises relative to the breaks, on the basis of the first information;
 determining the ratio between the aerobic exercise time of the plurality of aerobic exercises selected by the exercise selecting unit, and the break time of at least one of the plurality of breaks, on the basis of the exercise experience information acquired by the acquiring unit;
 determining the ratio between the anaerobic exercise time of the anaerobic exercises selected by the exercise selecting unit, and the break time of at least one of plurality of breaks, on the basis of the physical fitness information acquired by the acquiring unit; and
 generating a circuit exercise menu based on the plurality of selected exercises, the plurality of breaks and the ratios determined by the exercise ratio determining unit.

10. A computer implemented exercise support method comprising:
 acquiring on a computer first information representative of at least one of an exercise experience and physical fitness of a user;
 storing in a memory on the computer a plurality of kinds of exercises which includes at least one of an aerobic exercise and at least one of an anaerobic exercise;
 selecting a plurality of exercises which includes a plurality of aerobic exercises and a plurality of the anaerobic exercises stored in the memory, and a plurality of breaks;
 generating an exercise menu, including the plurality of selected exercises and the plurality of breaks;
 determining a ratio between each of break times of the breaks included in the exercise menu, and each of exercise times of the aerobic exercises and the anaerobic exercises relative to the breaks, on the basis of the first information;
 determining the ratio between the aerobic exercise time of the plurality of selected aerobic exercises, and the break time of at least one of the plurality of breaks, on the basis of the acquired exercise experience information;
 determining the ratio between the anaerobic exercise time of the plurality of selected anaerobic exercises and the break time of at least one of plurality of breaks, on the basis of the acquired physical fitness information; and
 generating a circuit exercise menu based on the plurality of selected exercises, the plurality of breaks and the determined ratios.

* * * * *